United States Patent [19]

Fitzmaurice et al.

[11] Patent Number: 5,539,093
[45] Date of Patent: Jul. 23, 1996

[54] DNA SEQUENCES ENCODING ENZYMES USEFUL IN CAROTENOID BIOSYNTHESIS

[76] Inventors: Wayne P. Fitzmaurice, 8064 Glengarriff Rd.; Gary M. Hellmann, 3516 Donegal Dr., both of Clemmons, N.C. 27012; Laurence K. Grill, 3570 Cantelow Rd., Vacaville, Calif. 95688; Monto H. Kumagai, 1330 Brown Dr., Davis, Calif. 95616; Guy R. della-Cioppa, 814 Derry Cir., Vacaville, Calif. 95688

[21] Appl. No.: 261,086

[22] Filed: Jun. 16, 1994

[51] Int. Cl.⁶ .................................................. C12N 15/53
[52] U.S. Cl. .............................................. 536/23.2; 435/189
[58] Field of Search ............................ 536/23.2; 435/189

[56] References Cited

U.S. PATENT DOCUMENTS

| | | | |
|---|---|---|---|
| 4,642,318 | 2/1987 | Wolff, K. | 514/560 |
| 5,304,478 | 4/1994 | Bird et al. | 435/172 |
| 5,328,845 | 7/1994 | Finkelstein et al. | 435/254 |

FOREIGN PATENT DOCUMENTS

| | | |
|---|---|---|
| 0393690 | 10/1990 | European Pat. Off. |
| 91/13078 | 9/1991 | WIPO |
| 9206206 | 4/1992 | WIPO |

OTHER PUBLICATIONS

Hugueney P., et al (1992) Eur. J. Biochem 209, 399–407.
Plekey, I. et al, (1992) Proc. Natl Acad. Sci. USA, 89, 4962–4966.
Linden, H., et al. (1993) Physiol. Plant 88, 229–236.
Seolnik, P. A. et al. (1993) Plant Physiol. 103, 1475.

*Primary Examiner*—Charles L. Patterson, Jr.

[57] ABSTRACT

DNA sequences isolated from Nicotiana species (e.g., *Nicotiana benthamiana* and *Nicotiana tabacum*) have SEQ ID NOS: 1, 3, 5 and 7. The DNA sequences encode polypeptides having enzymatic activity for producing zeta-carotene. The polypeptides are referred to as phytoene desaturase.

13 Claims, 1 Drawing Sheet

SEQUENCE LISTING ( 1 ) GENERAL INFORMATION:

( i i i ) NUMBER OF SEQUENCES: 8

( 2 ) INFORMATION FOR SEQ ID NO:1:

( i ) SEQUENCE CHARACTERISTICS:
        ( A ) LENGTH: 2095 base pairs
        ( B ) TYPE: nucleic acid
        ( C ) STRANDEDNESS: single
        ( D ) TOPOLOGY: linear (  i i  ) MOLECULE TYPE: cDNA (  i x  ) FEATURE:
    ( A ) NAME/KEY: CDS
    ( B ) LOCATION: 200..1945

(  x i  ) SEQUENCE DESCRIPTION: SEQ ID NO:1:

```
TATCTTTTTG TGGGTAACAG CCAAACCACC ACAAATTTTC AGTTCCCACT CTTAACTCTT        60

TTTAACTTCA ACACAACAAA TTTTTTGCTT TTCCTTCTTT GTTTATCTTG TGCATAACGA       120

TTTCCTACAA CTTTAGCATA ATCTTGGTTT GTAATCACAA CGTGAAACAC ATCACCTAGG       180

CGGTTTCATA CCGAGTAAA ATG CCC CAA ATT GGA CTT GTT TCT GCC GTT AAT       232
                     Met Pro Gln Ile Gly Leu Val Ser Ala Val Asn
                       1               5                      10

TTG AGA GTC CAA GGT AAT TCA GCT TAT CTT TGG AGC TCG AGG TCT TCT         280
Leu Arg Val Gln Gly Asn Ser Ala Tyr Leu Trp Ser Ser Arg Ser Ser
             15                  20                  25

TTG GGA ACT GAA AGT CAA GAT GGT CGC TTG CAA AGG AAT TTG TTA TGT         328
Leu Gly Thr Glu Ser Gln Asp Gly Arg Leu Gln Arg Asn Leu Leu Cys
         30                  35                  40

TTT GGT AGT AGC GAC TCC ATG GGG CAT AAG TTT AGA ATT CGT ACT CCC         376
Phe Gly Ser Ser Asp Ser Met Gly His Lys Phe Arg Ile Arg Thr Pro
     45                  50                  55

AGT GCC ATG ACC AGA AGA TTG ACA AAG GAC TTC AAT CCT TTA AAG GTA         424
Ser Ala Met Thr Arg Arg Leu Thr Lys Asp Phe Asn Pro Leu Lys Val
 60                  65                  70                  75

GTC TGC ATT GAT TAC CCA AGA CCG GAG CTA GAC AAT ACA GTT AAC TAT         472
Val Cys Ile Asp Tyr Pro Arg Pro Glu Leu Asp Asn Thr Val Asn Tyr
             80                  85                  90

TTG GAG GCG GCG TTA TCA TCA TCA TCA TTT CGT ACT TCC TCA CGC CCA         520
Leu Glu Ala Ala Leu Ser Ser Ser Ser Phe Arg Thr Ser Ser Arg Pro
                 95                 100                 105

ACA AAA CCA TTG GAG ATT GTT ATT GCT GGT GCA GGT TTG GGT GGC TTG         568
Thr Lys Pro Leu Glu Ile Val Ile Ala Gly Ala Gly Leu Gly Gly Leu
             110                 115                 120

TCT ACA GCA AAA TAT CTG GCA GAT GCT GGT CAC AAA CCG ATA TTG CTG         616
Ser Thr Ala Lys Tyr Leu Ala Asp Ala Gly His Lys Pro Ile Leu Leu
     125                 130                 135

GAG GCA AGA GAT GTC CTA GGT GGA AAG GTA GCT GCA TGG AAA GAT GAT         664
Glu Ala Arg Asp Val Leu Gly Gly Lys Val Ala Ala Trp Lys Asp Asp
 140                 145                 150                 155

GAT GGA GAT TGG TAC GAG ACT GGG TTG CAC ATA TTC TTT GGG GCT TAC         712
Asp Gly Asp Trp Tyr Glu Thr Gly Leu His Ile Phe Phe Gly Ala Tyr
                 160                 165                 170

CCA AAT ATG CAG AAC CTG TTT GGA GAA CTA GGG ATT AAC GAT CGG TTG         760
Pro Asn Met Gln Asn Leu Phe Gly Glu Leu Gly Ile Asn Asp Arg Leu
             175                 180                 185

CAG TGG AAG GAA CAT TCG ATG ATA TTT GCG ATG CCT AAC AAG CCG GGG         808
Gln Trp Lys Glu His Ser Met Ile Phe Ala Met Pro Asn Lys Pro Gly
     190                 195                 200

GAG TTC AGC CGC TTT GAT TTT CCT GAA GCT CTT CCT GCG CCA TTA AAT         856
Glu Phe Ser Arg Phe Asp Phe Pro Glu Ala Leu Pro Ala Pro Leu Asn
 205                 210                 215

GGA ATT TTA GCC ATA CTA AAG AAC AAC GAA ATG CTT ACA TGG GCC CGA         904
Gly Ile Leu Ala Ile Leu Lys Asn Asn Glu Met Leu Thr Trp Ala Arg
220                  225                 230                 235

AAA ATC AAA TTT GCT ATT GGA CTC TTG CCA GCA ATG CTT GGA GGG CAA         952
Lys Ile Lys Phe Ala Ile Gly Leu Leu Pro Ala Met Leu Gly Gly Gln
                 240                 245                 250

TCT TAT GTT GAA GCT CAA GAC GGT TTA AGT GTT AAG GAC TGG ATG AGA        1000
Ser Tyr Val Glu Ala Gln Asp Gly Leu Ser Val Lys Asp Trp Met Arg
```

-continued

|  |  |  |  |  |  |  |  |  | 255 |  |  | 260 |  |  | 265 |  |  |  |
|---|---|---|---|---|---|---|---|---|---|---|---|---|---|---|---|---|---|---|

```
AAG CAA GGT GTG CCT GAT AGG GTG ACA GAT GAG GTG TTC ATT GCC ATG      1048
Lys Gln Gly Val Pro Asp Arg Val Thr Asp Glu Val Phe Ile Ala Met
        270                 275                 280

TCA AAG GCA CTT AAC TTC ATA AAC CCT GAC GAG CTT TCC ATG CAG TGC      1096
Ser Lys Ala Leu Asn Phe Ile Asn Pro Asp Glu Leu Ser Met Gln Cys
    285                 290                 295

ATT TTG ATT GCT TTG AAC CAA TTT CTT CAG GAG AAA CAT GGT TCA AAA      1144
Ile Leu Ile Ala Leu Asn Gln Phe Leu Gln Glu Lys His Gly Ser Lys
300                 305                 310                 315

ATG GCC TTT TTA GAT GGT AAT CCT CCT GAG AGA CTT TGC ATG CCA ATT      1192
Met Ala Phe Leu Asp Gly Asn Pro Pro Glu Arg Leu Cys Met Pro Ile
            320                 325                 330

GTT GAA CAT ATT GAG TCA AAA GGT GGC CAA GTC AGA CTA AAC TCA CGA      1240
Val Glu His Ile Glu Ser Lys Gly Gly Gln Val Arg Leu Asn Ser Arg
                335                 340                 345

ATA AAA AAG ATT GAG CTG AAT GAG GAT GGA AGT GTC AAA TGT TTT ATA      1288
Ile Lys Lys Ile Glu Leu Asn Glu Asp Gly Ser Val Lys Cys Phe Ile
        350                 355                 360

CTG AAT AAT GGC AGT ACA ATT AAA GGA GAT GCT TTT GTG TTT GCC ACT      1336
Leu Asn Asn Gly Ser Thr Ile Lys Gly Asp Ala Phe Val Phe Ala Thr
    365                 370                 375

CCA GTG GAT ATC TTC AAG CTT CTT TTG CCT GAA GAC TGG AAA GAG ATC      1384
Pro Val Asp Ile Phe Lys Leu Leu Leu Pro Glu Asp Trp Lys Glu Ile
380                 385                 390                 395

CCA TAT TTC CAA AAG TTG GAG AAG CTA GTG GGA GTT CCT GTG ATA AAT      1432
Pro Tyr Phe Gln Lys Leu Glu Lys Leu Val Gly Val Pro Val Ile Asn
            400                 405                 410

GTC CAT ATA TGG TTT GAC AGA AAA CTG AAG AAC ACA TCT GAT AAT CTG      1480
Val His Ile Trp Phe Asp Arg Lys Leu Lys Asn Thr Ser Asp Asn Leu
                415                 420                 425

CTC TTC AGC AGA AGC CCA TTG CTC AGT GTG TAT GCT GAC TTG TCT GTT      1528
Leu Phe Ser Arg Ser Pro Leu Leu Ser Val Tyr Ala Asp Leu Ser Val
        430                 435                 440

ACA TGT AAG GAA TAT TAC AAC CCC AAT CAG TCT ATG TTG GAA TTG GTA      1576
Thr Cys Lys Glu Tyr Tyr Asn Pro Asn Gln Ser Met Leu Glu Leu Val
    445                 450                 455

TTT GCA CCT GCA GAA GAG TGG ATA AAT CGT AGT GAC TCA GAA ATT ATT      1624
Phe Ala Pro Ala Glu Glu Trp Ile Asn Arg Ser Asp Ser Glu Ile Ile
460                 465                 470                 475

GAT GCT ACA ATG AAG GAA CTA GCA AAG CTT TTC CCT GAC GAA ATT TCG      1672
Asp Ala Thr Met Lys Glu Leu Ala Lys Leu Phe Pro Asp Glu Ile Ser
            480                 485                 490

GCA GAT CAG AGC AAA GCA AAA ATA TCG AAG TAT CAT GTT GTC AAA ACT      1720
Ala Asp Gln Ser Lys Ala Lys Ile Ser Lys Tyr His Val Val Lys Thr
                495                 500                 505

CCA AGG TCT GTT TAT AAA ACT GTG CCA GGT TGT GAA CCC TGT CGG CCC      1768
Pro Arg Ser Val Tyr Lys Thr Val Pro Gly Cys Glu Pro Cys Arg Pro
        510                 515                 520

TTG CAA AGA TCT CCT ATT GAG GGG TTT TAT TTA GCT GGC GAC TAC ACA      1816
Leu Gln Arg Ser Pro Ile Glu Gly Phe Tyr Leu Ala Gly Asp Tyr Thr
    525                 530                 535

AAA CAG AAA TAC TTG GCT TCA ATG GAA GGT GCT GTC TTA TCA GGA AAG      1864
Lys Gln Lys Tyr Leu Ala Ser Met Glu Gly Ala Val Leu Ser Gly Lys
540                 545                 550                 555

CTT TGT GCC CAA GCT ATT GTA CAG GAT TAC GAG TTA CTT CTT GGC CGG      1912
Leu Cys Ala Gln Ala Ile Val Gln Asp Tyr Glu Leu Leu Leu Gly Arg
            560                 565                 570

AGC CAG AAG AAG TTG GCA GAA GCA AGC GTA GTT TAGCATGGTG AACTAAAATG    1965
Ser Gln Lys Lys Leu Ala Glu Ala Ser Val Val
```

|             |             | 575         |             | 580         |             |             |      |
|-------------|-------------|-------------|-------------|-------------|-------------|-------------|------|
| TTGCTTCTCT  | ACACTAAATT  | TAAGATGAAG  | GTGGCCACAC  | TGAATTAGCG  | TTGTAGACAA  |             | 2025 |
| CACATACAAG  | GACAGTACAA  | CATTTAACCC  | AAATACGAGA  | AATGTTACAC  | AAATAAAAAA  |             | 2085 |
| AAAAAAAAAA  |             |             |             |             |             |             | 2095 |

( 2 ) INFORMATION FOR SEQ ID NO:2:

( i ) SEQUENCE CHARACTERISTICS:
        ( A ) LENGTH: 582 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met Pro Gln Ile Gly Leu Val Ser Ala Val Asn Leu Arg Val Gln Gly
 1               5                  10                  15

Asn Ser Ala Tyr Leu Trp Ser Ser Arg Ser Ser Leu Gly Thr Glu Ser
            20                  25                  30

Gln Asp Gly Arg Leu Gln Arg Asn Leu Leu Cys Phe Gly Ser Ser Asp
        35                  40                  45

Ser Met Gly His Lys Phe Arg Ile Arg Thr Pro Ser Ala Met Thr Arg
    50                  55                  60

Arg Leu Thr Lys Asp Phe Asn Pro Leu Lys Val Val Cys Ile Asp Tyr
65                  70                  75                  80

Pro Arg Pro Glu Leu Asp Asn Thr Val Asn Tyr Leu Glu Ala Ala Leu
                85                  90                  95

Ser Ser Ser Ser Phe Arg Thr Ser Ser Arg Pro Thr Lys Pro Leu Glu
            100                 105                 110

Ile Val Ile Ala Gly Ala Gly Gly Leu Ser Thr Ala Lys Tyr
        115                 120                 125

Leu Ala Asp Ala Gly His Lys Pro Ile Leu Leu Glu Ala Arg Asp Val
    130                 135                 140

Leu Gly Gly Lys Val Ala Ala Trp Lys Asp Asp Gly Asp Trp Tyr
145                 150                 155                 160

Glu Thr Gly Leu His Ile Phe Phe Gly Ala Tyr Pro Asn Met Gln Asn
                165                 170                 175

Leu Phe Gly Glu Leu Gly Ile Asn Asp Arg Leu Gln Trp Lys Glu His
            180                 185                 190

Ser Met Ile Phe Ala Met Pro Asn Lys Pro Gly Glu Phe Ser Arg Phe
        195                 200                 205

Asp Phe Pro Glu Ala Leu Pro Ala Pro Leu Asn Gly Ile Leu Ala Ile
    210                 215                 220

Leu Lys Asn Asn Glu Met Leu Thr Trp Ala Arg Lys Ile Lys Phe Ala
225                 230                 235                 240

Ile Gly Leu Leu Pro Ala Met Leu Gly Gly Gln Ser Tyr Val Glu Ala
                245                 250                 255

Gln Asp Gly Leu Ser Val Lys Asp Trp Met Arg Lys Gln Gly Val Pro
            260                 265                 270

Asp Arg Val Thr Asp Glu Val Phe Ile Ala Met Ser Lys Ala Leu Asn
        275                 280                 285

Phe Ile Asn Pro Asp Glu Leu Ser Met Gln Cys Ile Leu Ile Ala Leu
    290                 295                 300

Asn Gln Phe Leu Gln Glu Lys His Gly Ser Lys Met Ala Phe Leu Asp
305                 310                 315                 320
```

| | | | | | | | | | | | | | | |
|---|---|---|---|---|---|---|---|---|---|---|---|---|---|---|
| Gly | Asn | Pro | Pro | Glu | Arg | Leu | Cys | Met | Pro | Ile | Val | Glu | His | Ile | Glu |
| | | | | 325 | | | | | 330 | | | | | 335 | |
| Ser | Lys | Gly | Gly | Gln | Val | Arg | Leu | Asn | Ser | Arg | Ile | Lys | Lys | Ile | Glu |
| | | | 340 | | | | | 345 | | | | | 350 | | |
| Leu | Asn | Glu | Asp | Gly | Ser | Val | Lys | Cys | Phe | Ile | Leu | Asn | Asn | Gly | Ser |
| | | | 355 | | | | | 360 | | | | | 365 | | |
| Thr | Ile | Lys | Gly | Asp | Ala | Phe | Val | Phe | Ala | Thr | Pro | Val | Asp | Ile | Phe |
| | 370 | | | | | 375 | | | | | 380 | | | | |
| Lys | Leu | Leu | Leu | Pro | Glu | Asp | Trp | Lys | Glu | Ile | Pro | Tyr | Phe | Gln | Lys |
| 385 | | | | | 390 | | | | | 395 | | | | | 400 |
| Leu | Glu | Lys | Leu | Val | Gly | Val | Pro | Val | Ile | Asn | Val | His | Ile | Trp | Phe |
| | | | | 405 | | | | | 410 | | | | | 415 | |
| Asp | Arg | Lys | Leu | Lys | Asn | Thr | Ser | Asp | Asn | Leu | Leu | Phe | Ser | Arg | Ser |
| | | | 420 | | | | | 425 | | | | | 430 | | |
| Pro | Leu | Leu | Ser | Val | Tyr | Ala | Asp | Leu | Ser | Val | Thr | Cys | Lys | Glu | Tyr |
| | | | 435 | | | | | 440 | | | | | 445 | | |
| Tyr | Asn | Pro | Asn | Gln | Ser | Met | Leu | Glu | Leu | Val | Phe | Ala | Pro | Ala | Glu |
| | | 450 | | | | | 455 | | | | | 460 | | | |
| Glu | Trp | Ile | Asn | Arg | Ser | Asp | Ser | Glu | Ile | Ile | Asp | Ala | Thr | Met | Lys |
| 465 | | | | | 470 | | | | | 475 | | | | | 480 |
| Glu | Leu | Ala | Lys | Leu | Phe | Pro | Asp | Glu | Ile | Ser | Ala | Asp | Gln | Ser | Lys |
| | | | | 485 | | | | | 490 | | | | | 495 | |
| Ala | Lys | Ile | Ser | Lys | Tyr | His | Val | Val | Lys | Thr | Pro | Arg | Ser | Val | Tyr |
| | | | 500 | | | | | 505 | | | | | 510 | | |
| Lys | Thr | Val | Pro | Gly | Cys | Glu | Pro | Cys | Arg | Pro | Leu | Gln | Arg | Ser | Pro |
| | | 515 | | | | | 520 | | | | | 525 | | | |
| Ile | Glu | Gly | Phe | Tyr | Leu | Ala | Gly | Asp | Tyr | Thr | Lys | Gln | Lys | Tyr | Leu |
| | 530 | | | | | 535 | | | | | 540 | | | | |
| Ala | Ser | Met | Glu | Gly | Ala | Val | Leu | Ser | Gly | Lys | Leu | Cys | Ala | Gln | Ala |
| 545 | | | | | 550 | | | | | 555 | | | | | 560 |
| Ile | Val | Gln | Asp | Tyr | Glu | Leu | Leu | Leu | Gly | Arg | Ser | Gln | Lys | Lys | Leu |
| | | | | 565 | | | | | 570 | | | | | 575 | |
| Ala | Glu | Ala | Ser | Val | Val | | | | | | | | | | |
| | | | | 580 | | | | | | | | | | | |

( 2 ) INFORMATION FOR SEQ ID NO:3:

( i ) SEQUENCE CHARACTERISTICS:
        ( A ) LENGTH: 2224 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 335..2080

( x i ) SEQUENCE DESCRIPTION: SEQ ID NO:3:

```
AAATAGCAAA  CAAATGATCC  GTTAACAGAA  GTGGCCAAAC  CCCCAAATTC  AGGCATCTCC        60

ACCAAATATT  AGTTTTTTAT  ACACAAAAGA  TTCAACACAA  ACAGTTAAGT  ACTTCTTTAA       120

TCGTCCTAAT  TCTTTGCTTC  AGGGGTATCT  TTTTTGTGGG  TAACGGCCAA  ACCACCACAA       180

ATTTTCAGTT  CCCACTCTTA  ACTCTTTCAA  CTTCAACACA  ACAAATTAGT  ATTTGCTTTT      240

CCTTCTTTGC  TTATCTAGTG  CATAACGATT  TTCTACAACT  TTAGCATAAT  CCACAACGTG      300

AAACACAACT  CCTTGGCGGT  TTATACCGAG  TAAA ATG CCC CAA ATT GGA CTT           352
                                      Met Pro Gln Ile Gly Leu
```

|     |     |     |     |     |     |     |     |     |     |     |     |     |     |     |     |     |
|---|---|---|---|---|---|---|---|---|---|---|---|---|---|---|---|---|
| GTT | TCT | GCC | GTT | AAT | TTG | AGA | GTC | CAA | GGT | AAT | TCA | GCT | TAT | CTT | TGG | 400 |
| Val | Ser | Ala | Val | Asn | Leu | Arg | Val | Gln | Gly | Asn | Ser | Ala | Tyr | Leu | Trp | |
|     |     |     | 10  |     |     |     |     | 15  |     |     |     |     | 20  |     |     | |
| AGC | TCG | AGG | TCT | TCG | TTG | GGA | ACT | GAA | AGT | CAA | GAT | GTT | TGC | TTG | CAA | 448 |
| Ser | Ser | Arg | Ser | Ser | Leu | Gly | Thr | Glu | Ser | Gln | Asp | Val | Cys | Leu | Gln | |
|     |     | 25  |     |     |     |     | 30  |     |     |     |     | 35  |     |     |     | |
| AGG | AAT | TTG | TTA | TGT | TTT | GGT | AGT | AGC | GAC | TCC | ATG | GGG | CAT | AAG | TTA | 496 |
| Arg | Asn | Leu | Leu | Cys | Phe | Gly | Ser | Ser | Asp | Ser | Met | Gly | His | Lys | Leu | |
|     | 40  |     |     |     |     | 45  |     |     |     |     | 50  |     |     |     |     | |
| AGG | ATT | CGT | ACT | CCA | AGT | GCC | ACG | ACC | CGA | AGA | TTG | ACA | AAG | GAC | TTT | 544 |
| Arg | Ile | Arg | Thr | Pro | Ser | Ala | Thr | Thr | Arg | Arg | Leu | Thr | Lys | Asp | Phe | |
| 55  |     |     |     |     | 60  |     |     |     |     | 65  |     |     |     |     | 70  | |
| AAT | CCT | TTA | AAG | GTA | GTC | TGC | ATT | GAT | TAT | CCA | AGA | CCA | GAG | CTA | GAC | 592 |
| Asn | Pro | Leu | Lys | Val | Val | Cys | Ile | Asp | Tyr | Pro | Arg | Pro | Glu | Leu | Asp | |
|     |     |     |     | 75  |     |     |     |     | 80  |     |     |     |     | 85  |     | |
| AAT | ACA | GTT | AAC | TAT | TTG | GAG | GCG | GCG | TTA | TTA | TCA | TCA | TCG | TTT | CGT | 640 |
| Asn | Thr | Val | Asn | Tyr | Leu | Glu | Ala | Ala | Leu | Leu | Ser | Ser | Ser | Phe | Arg | |
|     |     |     | 90  |     |     |     |     | 95  |     |     |     |     | 100 |     |     | |
| ACT | TCC | TCA | CGC | CCA | ACT | AAA | CCA | TTG | GAG | ATT | GTT | ATT | GCT | GGT | GCA | 688 |
| Thr | Ser | Ser | Arg | Pro | Thr | Lys | Pro | Leu | Glu | Ile | Val | Ile | Ala | Gly | Ala | |
|     |     | 105 |     |     |     |     | 110 |     |     |     |     | 115 |     |     |     | |
| GGT | TTG | GGT | GGC | TTG | TCT | ACA | GCA | AAA | TAT | CTG | GCA | GAT | GCT | GGT | CAC | 736 |
| Gly | Leu | Gly | Gly | Leu | Ser | Thr | Ala | Lys | Tyr | Leu | Ala | Asp | Ala | Gly | His | |
|     | 120 |     |     |     |     | 125 |     |     |     |     | 130 |     |     |     |     | |
| AAA | CCG | ATA | TTG | CTG | GAG | GCA | AGA | GAT | GTC | CTA | GGT | GGG | AAG | GTA | GCT | 784 |
| Lys | Pro | Ile | Leu | Leu | Glu | Ala | Arg | Asp | Val | Leu | Gly | Gly | Lys | Val | Ala | |
| 135 |     |     |     |     | 140 |     |     |     |     | 145 |     |     |     |     | 150 | |
| GCA | TGG | AAA | GAT | GAT | GAT | GGA | GAT | TGG | TAC | GAG | ACT | GGG | TTG | CAC | ATA | 832 |
| Ala | Trp | Lys | Asp | Asp | Asp | Gly | Asp | Trp | Tyr | Glu | Thr | Gly | Leu | His | Ile | |
|     |     |     |     | 155 |     |     |     |     | 160 |     |     |     |     | 165 |     | |
| TTC | TTT | GGG | GCT | TAC | CCA | AAT | ATG | CAG | AAC | CTG | TTT | GGA | GAA | CTA | GGG | 880 |
| Phe | Phe | Gly | Ala | Tyr | Pro | Asn | Met | Gln | Asn | Leu | Phe | Gly | Glu | Leu | Gly | |
|     |     |     | 170 |     |     |     |     | 175 |     |     |     |     | 180 |     |     | |
| ATT | GAT | GAT | CGG | TTG | CAG | TGG | AAG | GAA | CAT | TCA | ATG | ATA | TTT | GCG | ATG | 928 |
| Ile | Asp | Asp | Arg | Leu | Gln | Trp | Lys | Glu | His | Ser | Met | Ile | Phe | Ala | Met | |
|     |     | 185 |     |     |     |     | 190 |     |     |     |     | 195 |     |     |     | |
| CCT | AAC | AAG | CCA | GGG | GAG | TTC | AGC | CGC | TTT | GAT | TTT | CCT | GGA | GCT | CTT | 976 |
| Pro | Asn | Lys | Pro | Gly | Glu | Phe | Ser | Arg | Phe | Asp | Phe | Pro | Gly | Ala | Leu | |
|     | 200 |     |     |     |     | 205 |     |     |     |     | 210 |     |     |     |     | |
| CCT | GCG | CCA | TTA | AAT | GGA | ATT | TTG | GCC | ATA | CTA | AAG | AAC | AAC | GAA | ATG | 1024 |
| Pro | Ala | Pro | Leu | Asn | Gly | Ile | Leu | Ala | Ile | Leu | Lys | Asn | Asn | Glu | Met | |
| 215 |     |     |     |     | 220 |     |     |     |     | 225 |     |     |     |     | 230 | |
| CTT | ACG | TGG | CCC | GAG | AAA | GTC | AAA | TTT | GCT | ATT | GGA | CTC | TTG | CCA | GCA | 1072 |
| Leu | Thr | Trp | Pro | Glu | Lys | Val | Lys | Phe | Ala | Ile | Gly | Leu | Leu | Pro | Ala | |
|     |     |     |     | 235 |     |     |     |     | 240 |     |     |     |     | 245 |     | |
| ATG | CTT | GGA | GGG | CAA | TCT | TAT | GTT | GAA | GCT | CAA | GAC | GGT | TTA | AGT | GTT | 1120 |
| Met | Leu | Gly | Gly | Gln | Ser | Tyr | Val | Glu | Ala | Gln | Asp | Gly | Leu | Ser | Val | |
|     |     |     | 250 |     |     |     |     | 255 |     |     |     |     | 260 |     |     | |
| AAG | GAC | TGG | ATG | AGA | AAG | CAA | GGT | GTG | CCT | GAT | AGG | GTG | ACA | GAT | GAG | 1168 |
| Lys | Asp | Trp | Met | Arg | Lys | Gln | Gly | Val | Pro | Asp | Arg | Val | Thr | Asp | Glu | |
|     |     | 265 |     |     |     |     | 270 |     |     |     |     | 275 |     |     |     | |
| GTG | TCC | ATT | GCC | ATG | TCA | AAG | GCA | CTT | AAC | TTC | ATA | AAC | CCT | GAC | GAG | 1216 |
| Val | Ser | Ile | Ala | Met | Ser | Lys | Ala | Leu | Asn | Phe | Ile | Asn | Pro | Asp | Glu | |
|     |     | 280 |     |     |     |     | 285 |     |     |     |     | 290 |     |     |     | |
| CTT | TCG | ATG | CAG | TGC | ATT | TTG | ATT | GCT | TTG | AAC | AGA | TTT | CTT | CAG | GAG | 1264 |
| Leu | Ser | Met | Gln | Cys | Ile | Leu | Ile | Ala | Leu | Asn | Arg | Phe | Leu | Gln | Glu | |
| 295 |     |     |     |     | 300 |     |     |     |     | 305 |     |     |     |     | 310 | |
| AAA | CAT | GGT | TCA | AAA | ATG | GCC | TTT | TTA | GAT | GGT | AAC | CCT | CCT | GAG | AGA | 1312 |
| Lys | His | Gly | Ser | Lys | Met | Ala | Phe | Leu | Asp | Gly | Asn | Pro | Pro | Glu | Arg | |

-continued

|     |     |     |     |     | 315 |     |     |     | 320 |     |     |     | 325 |     |      |
|-----|-----|-----|-----|-----|-----|-----|-----|-----|-----|-----|-----|-----|-----|-----|------|
| CTT | TGC | ATG | CCG | ATT | GTG | GAA | CAT | ATT | GAG | TCA | AAA | GGT | GGC | CAA | GTC  | 1360 |
| Leu | Cys | Met | Pro | Ile | Val | Glu | His | Ile | Glu | Ser | Lys | Gly | Gly | Gln | Val  |
|     |     |     | 330 |     |     |     |     | 335 |     |     |     |     | 340 |     |      |
| AGA | CTA | AAC | TCA | CGA | ATA | AAA | AAG | ATC | GAG | CTG | AAT | GAG | GAT | GGA | AGT  | 1408 |
| Arg | Leu | Asn | Ser | Arg | Ile | Lys | Lys | Ile | Glu | Leu | Asn | Glu | Asp | Gly | Ser  |
|     |     |     | 345 |     |     |     | 350 |     |     |     |     | 355 |     |     |      |
| GTC | AAA | TGT | TTT | ATA | CTG | AAT | AAT | GGC | AGT | ACA | ATT | AAA | GGA | GAT | GCT  | 1456 |
| Val | Lys | Cys | Phe | Ile | Leu | Asn | Asn | Gly | Ser | Thr | Ile | Lys | Gly | Asp | Ala  |
|     | 360 |     |     |     |     | 365 |     |     |     |     | 370 |     |     |     |      |
| TTT | GTG | TTT | GCC | ACT | CCA | GTG | GAT | ATC | TTG | AAG | CTT | CTT | TTG | CCT | GAA  | 1504 |
| Phe | Val | Phe | Ala | Thr | Pro | Val | Asp | Ile | Leu | Lys | Leu | Leu | Leu | Pro | Glu  |
| 375 |     |     |     |     | 380 |     |     |     | 385 |     |     |     |     | 390 |      |
| GAC | TGG | AAA | GAG | ATC | CCA | TAT | TTC | CAA | AAG | TTG | GAG | AAG | CTA | GTG | GGA  | 1552 |
| Asp | Trp | Lys | Glu | Ile | Pro | Tyr | Phe | Gln | Lys | Leu | Glu | Lys | Leu | Val | Gly  |
|     |     |     |     | 395 |     |     |     | 400 |     |     |     |     | 405 |     |      |
| GTT | CCT | GTG | ATA | AAT | GTC | CAT | ATA | TGG | TTT | GAC | AGA | AAA | CTG | AAG | AAC  | 1600 |
| Val | Pro | Val | Ile | Asn | Val | His | Ile | Trp | Phe | Asp | Arg | Lys | Leu | Lys | Asn  |
|     |     |     | 410 |     |     |     | 415 |     |     |     |     | 420 |     |     |      |
| ACA | TCT | GAT | AAT | CTG | CTC | TTC | AGC | AGA | AGC | CCG | TTG | CTC | AGT | GTG | TAC  | 1648 |
| Thr | Ser | Asp | Asn | Leu | Leu | Phe | Ser | Arg | Ser | Pro | Leu | Leu | Ser | Val | Tyr  |
|     |     | 425 |     |     |     |     | 430 |     |     |     |     | 435 |     |     |      |
| GCT | GAC | ATG | TCT | GTT | ACA | TGT | AAG | GAA | TAT | TAC | AAC | CCC | AAT | CAG | TCT  | 1696 |
| Ala | Asp | Met | Ser | Val | Thr | Cys | Lys | Glu | Tyr | Tyr | Asn | Pro | Asn | Gln | Ser  |
|     | 440 |     |     |     |     | 445 |     |     |     |     | 450 |     |     |     |      |
| ATG | TTG | GAA | TTG | GTA | TTT | GCA | CCC | GCA | GAA | GAG | TGG | ATA | AAT | CGT | AGT  | 1744 |
| Met | Leu | Glu | Leu | Val | Phe | Ala | Pro | Ala | Glu | Glu | Trp | Ile | Asn | Arg | Ser  |
| 455 |     |     |     |     | 460 |     |     |     | 465 |     |     |     |     | 470 |      |
| GAC | TCA | GAA | ATT | ATT | GAT | GCT | ACA | ATG | AAG | GAA | CTA | GGC | AAG | CTT | TTC  | 1792 |
| Asp | Ser | Glu | Ile | Ile | Asp | Ala | Thr | Met | Lys | Glu | Leu | Gly | Lys | Leu | Phe  |
|     |     |     |     | 475 |     |     |     | 480 |     |     |     |     | 485 |     |      |
| CCT | GAT | GAA | ATT | TCG | GCA | GAT | CAG | AGC | AAA | GCA | AAA | ATA | TTG | AAG | TAT  | 1840 |
| Pro | Asp | Glu | Ile | Ser | Ala | Asp | Gln | Ser | Lys | Ala | Lys | Ile | Leu | Lys | Tyr  |
|     |     |     | 490 |     |     |     | 495 |     |     |     |     | 500 |     |     |      |
| CAT | GTT | GTC | AAA | ACC | CCA | AGG | TCT | GTT | TAT | AAA | ACT | GTG | CCA | GGT | TGT  | 1888 |
| His | Val | Val | Lys | Thr | Pro | Arg | Ser | Val | Tyr | Lys | Thr | Val | Pro | Gly | Cys  |
|     |     | 505 |     |     |     |     | 510 |     |     |     |     | 515 |     |     |      |
| GAA | CCC | TGT | CGG | CCC | TTG | CAA | AGA | TCC | CCT | ATA | GAG | GGT | TTT | TAT | TTA  | 1936 |
| Glu | Pro | Cys | Arg | Pro | Leu | Gln | Arg | Ser | Pro | Ile | Glu | Gly | Phe | Tyr | Leu  |
|     | 520 |     |     |     |     | 525 |     |     |     |     | 530 |     |     |     |      |
| GCT | GGT | GAC | TAC | ACG | AAA | CAG | AAG | TAC | TTG | GCT | TCA | ATG | GAA | GGT | GCT  | 1984 |
| Ala | Gly | Asp | Tyr | Thr | Lys | Gln | Lys | Tyr | Leu | Ala | Ser | Met | Glu | Gly | Ala  |
| 535 |     |     |     |     | 540 |     |     |     | 545 |     |     |     |     | 550 |      |
| GTC | TTA | TCA | GGA | AAG | CTT | TGT | GCC | GAA | GCT | ATT | GTA | CAG | GAT | TAC | GAG  | 2032 |
| Val | Leu | Ser | Gly | Lys | Leu | Cys | Ala | Glu | Ala | Ile | Val | Gln | Asp | Tyr | Glu  |
|     |     |     | 555 |     |     |     | 560 |     |     |     |     | 565 |     |     |      |
| TTA | CTT | CTT | GGA | CGG | AGC | CAG | AAG | ATG | TTG | GCA | GAA | GCA | AGC | GTA | GTT  | 2080 |
| Leu | Leu | Leu | Gly | Arg | Ser | Gln | Lys | Met | Leu | Ala | Glu | Ala | Ser | Val | Val  |
|     |     |     | 570 |     |     |     | 575 |     |     |     |     | 580 |     |     |      |

TAGCATAGTG AACTAAAATG TTAATTCTGT ACACAAAATT TAAGATGAAG GCGGCCACGC    2140

TGAATTAGCG TTGTACACAA CTTATACAAG CACAGTACAA CATTGAAACC AAATACGAGA    2200

AATGTTACAC AAAAAAAAAA AAAA    2224

( 2 ) INFORMATION FOR SEQ ID NO:4:

( i ) SEQUENCE CHARACTERISTICS:
            ( A ) LENGTH: 582 amino acids
            ( B ) TYPE: amino acid
            ( D ) TOPOLOGY: linear ( i i ) MOLECULE TYPE: protein ( x i ) SEQUENCE DESCRIPTION: SEQ ID NO:4:

| Met | Pro | Gln | Ile | Gly | Leu | Val | Ser | Ala | Val | Asn | Leu | Arg | Val | Gln | Gly |
| 1 | | | | 5 | | | | | 10 | | | | | 15 | |

| Asn | Ser | Ala | Tyr | Leu | Trp | Ser | Ser | Arg | Ser | Ser | Leu | Gly | Thr | Glu | Ser |
| | | | 20 | | | | | 25 | | | | | 30 | | |

| Gln | Asp | Val | Cys | Leu | Gln | Arg | Asn | Leu | Leu | Cys | Phe | Gly | Ser | Ser | Asp |
| | | 35 | | | | | 40 | | | | | 45 | | | |

| Ser | Met | Gly | His | Lys | Leu | Arg | Ile | Arg | Thr | Pro | Ser | Ala | Thr | Thr | Arg |
| | 50 | | | | | 55 | | | | | 60 | | | | |

| Arg | Leu | Thr | Lys | Asp | Phe | Asn | Pro | Leu | Lys | Val | Val | Cys | Ile | Asp | Tyr |
| 65 | | | | | 70 | | | | | 75 | | | | | 80 |

| Pro | Arg | Pro | Glu | Leu | Asp | Asn | Thr | Val | Asn | Tyr | Leu | Glu | Ala | Ala | Leu |
| | | | | 85 | | | | | 90 | | | | | 95 | |

| Leu | Ser | Ser | Ser | Phe | Arg | Thr | Ser | Ser | Arg | Pro | Thr | Lys | Pro | Leu | Glu |
| | | | 100 | | | | | 105 | | | | | 110 | | |

| Ile | Val | Ile | Ala | Gly | Ala | Gly | Leu | Gly | Gly | Leu | Ser | Thr | Ala | Lys | Tyr |
| | | 115 | | | | | 120 | | | | | 125 | | | |

| Leu | Ala | Asp | Ala | Gly | His | Lys | Pro | Ile | Leu | Leu | Glu | Ala | Arg | Asp | Val |
| | 130 | | | | | 135 | | | | | 140 | | | | |

| Leu | Gly | Gly | Lys | Val | Ala | Ala | Trp | Lys | Asp | Asp | Asp | Gly | Asp | Trp | Tyr |
| 145 | | | | | 150 | | | | | 155 | | | | | 160 |

| Glu | Thr | Gly | Leu | His | Ile | Phe | Phe | Gly | Ala | Tyr | Pro | Asn | Met | Gln | Asn |
| | | | | 165 | | | | | 170 | | | | | 175 | |

| Leu | Phe | Gly | Glu | Leu | Gly | Ile | Asp | Asp | Arg | Leu | Gln | Trp | Lys | Glu | His |
| | | | 180 | | | | | 185 | | | | | 190 | | |

| Ser | Met | Ile | Phe | Ala | Met | Pro | Asn | Lys | Pro | Gly | Glu | Phe | Ser | Arg | Phe |
| | | 195 | | | | | 200 | | | | | 205 | | | |

| Asp | Phe | Pro | Gly | Ala | Leu | Pro | Ala | Pro | Leu | Asn | Gly | Ile | Leu | Ala | Ile |
| | 210 | | | | | 215 | | | | | 220 | | | | |

| Leu | Lys | Asn | Asn | Glu | Met | Leu | Thr | Trp | Pro | Glu | Lys | Val | Lys | Phe | Ala |
| 225 | | | | | 230 | | | | | 235 | | | | | 240 |

| Ile | Gly | Leu | Leu | Pro | Ala | Met | Leu | Gly | Gly | Gln | Ser | Tyr | Val | Glu | Ala |
| | | | | 245 | | | | | 250 | | | | | 255 | |

| Gln | Asp | Gly | Leu | Ser | Val | Lys | Asp | Trp | Met | Arg | Lys | Gln | Gly | Val | Pro |
| | | | 260 | | | | | 265 | | | | | 270 | | |

| Asp | Arg | Val | Thr | Asp | Glu | Val | Ser | Ile | Ala | Met | Ser | Lys | Ala | Leu | Asn |
| | | 275 | | | | | 280 | | | | | 285 | | | |

| Phe | Ile | Asn | Pro | Asp | Glu | Leu | Ser | Met | Gln | Cys | Ile | Leu | Ile | Ala | Leu |
| | 290 | | | | | 295 | | | | | 300 | | | | |

| Asn | Arg | Phe | Leu | Gln | Glu | Lys | His | Gly | Ser | Lys | Met | Ala | Phe | Leu | Asp |
| 305 | | | | | 310 | | | | | 315 | | | | | 320 |

| Gly | Asn | Pro | Pro | Glu | Arg | Leu | Cys | Met | Pro | Ile | Val | Glu | His | Ile | Glu |
| | | | | 325 | | | | | 330 | | | | | 335 | |

| Ser | Lys | Gly | Gly | Gln | Val | Arg | Leu | Asn | Ser | Arg | Ile | Lys | Lys | Ile | Glu |
| | | | 340 | | | | | 345 | | | | | 350 | | |

| Leu | Asn | Glu | Asp | Gly | Ser | Val | Lys | Cys | Phe | Ile | Leu | Asn | Asn | Gly | Ser |
| | | 355 | | | | | 360 | | | | | 365 | | | |

| Thr | Ile | Lys | Gly | Asp | Ala | Phe | Val | Phe | Ala | Thr | Pro | Val | Asp | Ile | Leu |
| | 370 | | | | | 375 | | | | | 380 | | | | |

| Lys | Leu | Leu | Leu | Pro | Glu | Asp | Trp | Lys | Glu | Ile | Pro | Tyr | Phe | Gln | Lys |
| 385 | | | | | 390 | | | | | 395 | | | | | 400 |

| Leu | Glu | Lys | Leu | Val | Gly | Val | Pro | Val | Ile | Asn | Val | His | Ile | Trp | Phe |

|  | 405 |  |  |  |  |  |  | 410 |  |  |  |  |  | 415 |  |
|---|---|---|---|---|---|---|---|---|---|---|---|---|---|---|---|
| Asp | Arg | Lys | Leu | Lys | Asn | Thr | Ser | Asp | Asn | Leu | Leu | Phe | Ser | Arg | Ser |
|  |  |  | 420 |  |  |  |  | 425 |  |  |  | 430 |  |  |  |
| Pro | Leu | Leu | Ser | Val | Tyr | Ala | Asp | Met | Ser | Val | Thr | Cys | Lys | Glu | Tyr |
|  |  | 435 |  |  |  |  | 440 |  |  |  | 445 |  |  |  |  |
| Tyr | Asn | Pro | Asn | Gln | Ser | Met | Leu | Glu | Leu | Val | Phe | Ala | Pro | Ala | Glu |
|  | 450 |  |  |  |  | 455 |  |  |  |  | 460 |  |  |  |  |
| Glu | Trp | Ile | Asn | Arg | Ser | Asp | Ser | Glu | Ile | Ile | Asp | Ala | Thr | Met | Lys |
| 465 |  |  |  | 470 |  |  |  |  | 475 |  |  |  |  |  | 480 |
| Glu | Leu | Gly | Lys | Leu | Phe | Pro | Asp | Glu | Ile | Ser | Ala | Asp | Gln | Ser | Lys |
|  |  |  |  | 485 |  |  |  |  | 490 |  |  |  |  | 495 |  |
| Ala | Lys | Ile | Leu | Lys | Tyr | His | Val | Val | Lys | Thr | Pro | Arg | Ser | Val | Tyr |
|  |  |  | 500 |  |  |  |  | 505 |  |  |  | 510 |  |  |  |
| Lys | Thr | Val | Pro | Gly | Cys | Glu | Pro | Cys | Arg | Pro | Leu | Gln | Arg | Ser | Pro |
|  |  | 515 |  |  |  |  | 520 |  |  |  |  | 525 |  |  |  |
| Ile | Glu | Gly | Phe | Tyr | Leu | Ala | Gly | Asp | Tyr | Thr | Lys | Gln | Lys | Tyr | Leu |
|  | 530 |  |  |  |  | 535 |  |  |  |  | 540 |  |  |  |  |
| Ala | Ser | Met | Glu | Gly | Ala | Val | Leu | Ser | Gly | Lys | Leu | Cys | Ala | Glu | Ala |
| 545 |  |  |  |  | 550 |  |  |  |  | 555 |  |  |  |  | 560 |
| Ile | Val | Gln | Asp | Tyr | Glu | Leu | Leu | Leu | Gly | Arg | Ser | Gln | Lys | Met | Leu |
|  |  |  |  | 565 |  |  |  |  | 570 |  |  |  |  | 575 |  |
| Ala | Glu | Ala | Ser | Val | Val |  |  |  |  |  |  |  |  |  |  |
|  |  |  | 580 |  |  |  |  |  |  |  |  |  |  |  |  |

( 2 ) INFORMATION FOR SEQ ID NO:5:

( i ) SEQUENCE CHARACTERISTICS:
        ( A ) LENGTH: 1982 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 107..1852

( x i ) SEQUENCE DESCRIPTION: SEQ ID NO:5:

| TTCCTACAAC | TATAACATAG | TCTTGGTTTC | AGAATCCACA | ACTTGAAATA | CAACTCCTAG | 60 |
|---|---|---|---|---|---|---|

| GCGGTTTCAT | TCCGAGGCTT | AATTTACCGC | TATTTTGCTC | AGTAAA | ATG | CCC | CAA | 115 |
|---|---|---|---|---|---|---|---|---|
|  |  |  |  |  | Met | Pro | Gln |  |
|  |  |  |  |  | 1 |  |  |  |

| ATT | GGA | CTT | GTT | TCT | GCC | GTT | AAT | TTG | AGA | GTC | CAA | GGT | AAT | TCA | GCT | 163 |
|---|---|---|---|---|---|---|---|---|---|---|---|---|---|---|---|---|
| Ile | Gly | Leu | Val | Ser | Ala | Val | Asn | Leu | Arg | Val | Gln | Gly | Asn | Ser | Ala |  |
|  | 5 |  |  |  |  |  | 10 |  |  |  |  | 15 |  |  |  |  |

| TAT | CTT | TGG | AGC | TCG | AGG | TCT | TCG | TTG | GGA | ACT | GAA | AGT | CAA | GAT | GGT | 211 |
|---|---|---|---|---|---|---|---|---|---|---|---|---|---|---|---|---|
| Tyr | Leu | Trp | Ser | Ser | Arg | Ser | Ser | Leu | Gly | Thr | Glu | Ser | Gln | Asp | Gly |  |
| 20 |  |  |  |  | 25 |  |  |  |  | 30 |  |  |  |  | 35 |  |

| CGC | TTG | CAA | AGG | AAT | TTG | TTA | TGT | TTT | GGT | AGT | AGC | GAC | TCC | ATG | GGG | 259 |
|---|---|---|---|---|---|---|---|---|---|---|---|---|---|---|---|---|
| Arg | Leu | Gln | Arg | Asn | Leu | Leu | Cys | Phe | Gly | Ser | Ser | Asp | Ser | Met | Gly |  |
|  |  |  |  | 40 |  |  |  |  | 45 |  |  |  |  | 50 |  |  |

| CAT | AAG | TTA | AGG | ATT | CGT | ACT | CCC | AGT | GCC | ACG | ACC | AGA | AGA | TTG | ACA | 307 |
|---|---|---|---|---|---|---|---|---|---|---|---|---|---|---|---|---|
| His | Lys | Leu | Arg | Ile | Arg | Thr | Pro | Ser | Ala | Thr | Thr | Arg | Arg | Leu | Thr |  |
|  |  |  | 55 |  |  |  |  | 60 |  |  |  |  | 65 |  |  |  |

| AAG | GAC | TTT | AAT | CCT | TTA | AAG | GTA | GTC | TGC | ATT | GAT | TAT | CCA | AGA | CCA | 355 |
|---|---|---|---|---|---|---|---|---|---|---|---|---|---|---|---|---|
| Lys | Asp | Phe | Asn | Pro | Leu | Lys | Val | Val | Cys | Ile | Asp | Tyr | Pro | Arg | Pro |  |
|  |  | 70 |  |  |  |  | 75 |  |  |  |  | 80 |  |  |  |  |

| GAG | CTA | GAC | AAT | ACA | GTT | AAC | TAT | TTG | GAG | GCG | GCG | TTA | TTA | TCA | TCA | 403 |
|---|---|---|---|---|---|---|---|---|---|---|---|---|---|---|---|---|
| Glu | Leu | Asp | Asn | Thr | Val | Asn | Tyr | Leu | Glu | Ala | Ala | Leu | Leu | Ser | Ser |  |

|  | 85 |  |  |  |  | 90 |  |  |  |  | 95 |  |  |  |  |  |
|---|---|---|---|---|---|---|---|---|---|---|---|---|---|---|---|---|
| TCA | TTT | CGT | ACT | TCC | TCA | CGC | CCA | ACT | AAA | CCA | TTG | GAG | ATT | GTT | ATT | 451 |
| Ser | Phe | Arg | Thr | Ser | Ser | Arg | Pro | Thr | Lys | Pro | Leu | Glu | Ile | Val | Ile |  |
| 100 |  |  |  |  | 105 |  |  |  |  | 110 |  |  |  |  | 115 |  |
| GCT | GGT | GCA | GGT | TTG | GGT | GGT | TTG | TCT | ACA | GCA | AAA | TAT | CTG | GCA | GAT | 499 |
| Ala | Gly | Ala | Gly | Leu | Gly | Gly | Leu | Ser | Thr | Ala | Lys | Tyr | Leu | Ala | Asp |  |
|  |  |  |  | 120 |  |  |  |  | 125 |  |  |  |  | 130 |  |  |
| GCT | GGT | CAC | AAA | CCG | ATA | TTG | CTG | GAG | GCA | AGA | GAT | GTC | CTA | GGT | GGA | 547 |
| Ala | Gly | His | Lys | Pro | Ile | Leu | Leu | Glu | Ala | Arg | Asp | Val | Leu | Gly | Gly |  |
|  |  | 135 |  |  |  |  | 140 |  |  |  |  | 145 |  |  |  |  |
| AAG | GTA | GCT | GCA | TGG | AAA | GAT | GAT | GAT | GGA | GAT | TGG | TAT | GAG | ACT | GGG | 595 |
| Lys | Val | Ala | Ala | Trp | Lys | Asp | Asp | Asp | Gly | Asp | Trp | Tyr | Glu | Thr | Gly |  |
|  |  | 150 |  |  |  |  | 155 |  |  |  |  | 160 |  |  |  |  |
| TTG | CAT | ATA | TTC | TTT | GGG | GCT | TAC | CCA | AAT | ATG | CAG | AAC | CTG | TTT | GGA | 643 |
| Leu | His | Ile | Phe | Phe | Gly | Ala | Tyr | Pro | Asn | Met | Gln | Asn | Leu | Phe | Gly |  |
|  | 165 |  |  |  |  | 170 |  |  |  |  | 175 |  |  |  |  |  |
| GAA | CTA | GGG | ATT | AAC | GAT | CGA | TTG | CAG | TGG | AAG | GAA | CAT | TCA | ATG | ATA | 691 |
| Glu | Leu | Gly | Ile | Asn | Asp | Arg | Leu | Gln | Trp | Lys | Glu | His | Ser | Met | Ile |  |
| 180 |  |  |  |  | 185 |  |  |  |  | 190 |  |  |  |  | 195 |  |
| TTT | GCG | ATG | CCT | AAC | AAG | CCA | GGG | GAA | TTC | AGC | CGC | TTT | GAT | TTT | CCT | 739 |
| Phe | Ala | Met | Pro | Asn | Lys | Pro | Gly | Glu | Phe | Ser | Arg | Phe | Asp | Phe | Pro |  |
|  |  |  |  | 200 |  |  |  |  | 205 |  |  |  |  | 210 |  |  |
| GAA | GCT | CTT | CCT | GCG | CCA | TTA | AAT | GGA | ACT | TTG | GCC | ATA | CTA | AAG | AAC | 787 |
| Glu | Ala | Leu | Pro | Ala | Pro | Leu | Asn | Gly | Thr | Leu | Ala | Ile | Leu | Lys | Asn |  |
|  |  |  | 215 |  |  |  |  | 220 |  |  |  |  | 225 |  |  |  |
| AAT | GAA | ATG | CTT | ACA | TGG | CCC | GAA | AAA | GTC | AAA | TTT | GCT | ATT | GGA | CTC | 835 |
| Asn | Glu | Met | Leu | Thr | Trp | Pro | Glu | Lys | Val | Lys | Phe | Ala | Ile | Gly | Leu |  |
|  |  | 230 |  |  |  |  | 235 |  |  |  |  | 240 |  |  |  |  |
| TTG | CCA | GCA | ATG | CTT | GGA | GGG | CAA | TCT | TAT | GTT | GAA | GCT | CAA | GAC | GGT | 883 |
| Leu | Pro | Ala | Met | Leu | Gly | Gly | Gln | Ser | Tyr | Val | Glu | Ala | Gln | Asp | Gly |  |
|  | 245 |  |  |  |  | 250 |  |  |  |  | 255 |  |  |  |  |  |
| TTA | AGT | GTT | AAG | GAC | TGG | ATG | AGA | AAG | CAA | GGT | GTG | CCT | GAT | AGG | GTG | 931 |
| Leu | Ser | Val | Lys | Asp | Trp | Met | Arg | Lys | Gln | Gly | Val | Pro | Asp | Arg | Val |  |
| 260 |  |  |  |  | 265 |  |  |  |  | 270 |  |  |  |  | 275 |  |
| ACA | GAT | AAG | GTG | TTC | ATT | GCC | ATG | TCA | AAG | GCA | CTT | AAC | TTC | ATA | AAC | 979 |
| Thr | Asp | Lys | Val | Phe | Ile | Ala | Met | Ser | Lys | Ala | Leu | Asn | Phe | Ile | Asn |  |
|  |  |  |  | 280 |  |  |  |  | 285 |  |  |  |  | 290 |  |  |
| CCT | GAC | GAG | CTC | TCG | ATG | CAG | TGC | ATT | TTG | ATT | GCT | TTG | AAC | AGA | TTT | 1027 |
| Pro | Asp | Glu | Leu | Ser | Met | Gln | Cys | Ile | Leu | Ile | Ala | Leu | Asn | Arg | Phe |  |
|  |  |  | 295 |  |  |  |  | 300 |  |  |  |  | 305 |  |  |  |
| CTT | CAG | GAG | AAA | CAT | GGT | TCA | AAA | ATG | GCC | TTT | TTA | GAT | GGT | AAC | CCT | 1075 |
| Leu | Gln | Glu | Lys | His | Gly | Ser | Lys | Met | Ala | Phe | Leu | Asp | Gly | Asn | Pro |  |
|  |  | 310 |  |  |  |  | 315 |  |  |  |  | 320 |  |  |  |  |
| CCT | GAG | AGA | CTT | TGC | ATG | CCG | ATT | GTT | GAA | CAT | ATT | GAG | TCA | AAA | GGT | 1123 |
| Pro | Glu | Arg | Leu | Cys | Met | Pro | Ile | Val | Glu | His | Ile | Glu | Ser | Lys | Gly |  |
|  | 325 |  |  |  |  | 330 |  |  |  |  | 335 |  |  |  |  |  |
| GGC | CAA | GTC | AGA | CTA | AAC | TCA | CGA | ATA | AAA | AAG | ATT | GAG | CTC | AAT | GAG | 1171 |
| Gly | Gln | Val | Arg | Leu | Asn | Ser | Arg | Ile | Lys | Lys | Ile | Glu | Leu | Asn | Glu |  |
| 340 |  |  |  |  | 345 |  |  |  |  | 350 |  |  |  |  | 355 |  |
| GAT | GGA | AGT | GTC | AAA | TGT | TTT | ATA | CTG | AAT | AAT | GGC | AGT | ACA | ATT | AAA | 1219 |
| Asp | Gly | Ser | Val | Lys | Cys | Phe | Ile | Leu | Asn | Asn | Gly | Ser | Thr | Ile | Lys |  |
|  |  |  |  | 360 |  |  |  |  | 365 |  |  |  |  | 370 |  |  |
| GGA | GAT | GCT | TTT | GTG | TTT | GCC | ACT | CCA | GTG | GAT | ATC | TTC | AAG | CTT | CTT | 1267 |
| Gly | Asp | Ala | Phe | Val | Phe | Ala | Thr | Pro | Val | Asp | Ile | Phe | Lys | Leu | Leu |  |
|  |  |  | 375 |  |  |  |  | 380 |  |  |  |  | 385 |  |  |  |
| TTG | CCT | GAA | GAC | TGG | AAA | GAG | ATC | CCA | TAT | TTC | CAA | AAG | TTG | GAG | AAG | 1315 |
| Leu | Pro | Glu | Asp | Trp | Lys | Glu | Ile | Pro | Tyr | Phe | Gln | Lys | Leu | Glu | Lys |  |
|  |  | 390 |  |  |  |  | 395 |  |  |  |  | 400 |  |  |  |  |
| CTA | GTG | GGA | GTT | CCT | GTG | ATA | AAT | GTC | CAT | ATA | TGG | TTT | GAC | AGA | AAA | 1363 |
| Leu | Val | Gly | Val | Pro | Val | Ile | Asn | Val | His | Ile | Trp | Phe | Asp | Arg | Lys |  |

|     |     |     |     |     |     |     |     |     |     |     |     |     |     |     |     |      |
|-----|-----|-----|-----|-----|-----|-----|-----|-----|-----|-----|-----|-----|-----|-----|-----|------|
|     |     |     | 405 |     |     |     |     | 410 |     |     |     |     | 415 |     |     |      |
| CTG | AAG | AAC | ACA | TCT | GAT | AAT | CTG | CTC | TTC | AGC | AGA | AGT | CCA | CTG | CTC | 1411 |
| Leu | Lys | Asn | Thr | Ser | Asp | Asn | Leu | Leu | Phe | Ser | Arg | Ser | Pro | Leu | Leu |      |
| 420 |     |     |     |     | 425 |     |     |     |     | 430 |     |     |     |     | 435 |      |
| AGT | GTG | TAT | GCT | GAC | ATG | TCT | GTT | ACA | TGT | AAG | GAA | TAT | TAC | AAC | CCC | 1459 |
| Ser | Val | Tyr | Ala | Asp | Met | Ser | Val | Thr | Cys | Lys | Glu | Tyr | Tyr | Asn | Pro |      |
|     |     |     |     | 440 |     |     |     |     | 445 |     |     |     |     | 450 |     |      |
| AAT | CAG | TCT | ATG | TTG | GAA | TTG | GTA | TTT | GCA | CCT | GCA | GAA | GAG | TGG | ATA | 1507 |
| Asn | Gln | Ser | Met | Leu | Glu | Leu | Val | Phe | Ala | Pro | Ala | Glu | Glu | Trp | Ile |      |
|     |     |     | 455 |     |     |     |     | 460 |     |     |     |     | 465 |     |     |      |
| AAT | CGC | AGT | GAC | TCA | GAA | ATT | ATT | GAT | GCT | ACA | ATG | AAG | GAA | CTA | GCA | 1555 |
| Asn | Arg | Ser | Asp | Ser | Glu | Ile | Ile | Asp | Ala | Thr | Met | Lys | Glu | Leu | Ala |      |
|     |     | 470 |     |     |     | 475 |     |     |     |     | 480 |     |     |     |     |      |
| AAA | CTT | TTC | CCT | GAT | GAA | ATT | TCG | GCA | GAT | CAG | AGC | AAA | GCA | AAA | ATA | 1603 |
| Lys | Leu | Phe | Pro | Asp | Glu | Ile | Ser | Ala | Asp | Gln | Ser | Lys | Ala | Lys | Ile |      |
|     | 485 |     |     |     |     | 490 |     |     |     |     | 495 |     |     |     |     |      |
| TTG | AAG | TAT | CAT | GTT | GTC | AAA | ACT | CCA | AGG | TCT | GTT | TAT | AAA | ACT | GTG | 1651 |
| Leu | Lys | Tyr | His | Val | Val | Lys | Thr | Pro | Arg | Ser | Val | Tyr | Lys | Thr | Val |      |
| 500 |     |     |     |     | 505 |     |     |     |     | 510 |     |     |     |     | 515 |      |
| CCA | GGT | TGT | GAA | CTC | TGT | CGG | CCC | TTG | CAA | AGA | TCT | CCT | ATT | GAG | GGG | 1699 |
| Pro | Gly | Cys | Glu | Leu | Cys | Arg | Pro | Leu | Gln | Arg | Ser | Pro | Ile | Glu | Gly |      |
|     |     |     |     | 520 |     |     |     |     | 525 |     |     |     |     | 530 |     |      |
| TTT | TAT | TTA | GCT | GGT | GAC | TAC | ACG | AAA | CAG | AAG | TAC | TTG | GCT | TCA | ATG | 1747 |
| Phe | Tyr | Leu | Ala | Gly | Asp | Tyr | Thr | Lys | Gln | Lys | Tyr | Leu | Ala | Ser | Met |      |
|     |     |     | 535 |     |     |     |     |     | 540 |     |     |     | 545 |     |     |      |
| GAA | GGT | GCT | GTC | TTA | TCA | GGA | AAG | CTT | TGT | GCC | CAA | GCT | ATT | GTA | CAG | 1795 |
| Glu | Gly | Ala | Val | Leu | Ser | Gly | Lys | Leu | Cys | Ala | Gln | Ala | Ile | Val | Gln |      |
|     |     | 550 |     |     |     | 555 |     |     |     |     | 560 |     |     |     |     |      |
| GAT | TAC | GAG | TTA | CTT | CTT | GGC | CGG | AGC | CAG | AAG | AAG | TTG | GCA | GAA | GCA | 1843 |
| Asp | Tyr | Glu | Leu | Leu | Leu | Gly | Arg | Ser | Gln | Lys | Lys | Leu | Ala | Glu | Ala |      |
|     | 565 |     |     |     |     | 570 |     |     |     |     | 575 |     |     |     |     |      |
| AGC | GTA | GTT | TAGCATAGTG | AACTAAAGTG | TTGCTTCTGA | ATACTAAATT | | | | | | | | | | 1892 |
| Ser | Val | Val |     |     |     |     |     |     |     |     |     |     |     |     |     |      |
| 580 |     |     |     |     |     |     |     |     |     |     |     |     |     |     |     |      |

TAAGATGAAG GCGGCCACAC TGAATTAGCG TTGTACACAA CATATACAAG CACAGTACAA 1952

CATTGAACCC AAATACGAGA AATGTTACAC 1982

( 2 ) INFORMATION FOR SEQ ID NO:6:

( i ) SEQUENCE CHARACTERISTICS:
        ( A ) LENGTH: 582 amino acids
        ( B ) TYPE: amino acid
        ( D ) TOPOLOGY: linear ( i i ) MOLECULE TYPE: protein ( x i ) SEQUENCE DESCRIPTION: SEQ ID NO:6:

| Met | Pro | Gln | Ile | Gly | Leu | Val | Ser | Ala | Val | Asn | Leu | Arg | Val | Gln | Gly |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |
| Asn | Ser | Ala | Tyr | Leu | Trp | Ser | Ser | Arg | Ser | Ser | Leu | Gly | Thr | Glu | Ser |
|     |     |     | 20  |     |     |     |     | 25  |     |     |     |     | 30  |     |     |
| Gln | Asp | Gly | Arg | Leu | Gln | Arg | Asn | Leu | Leu | Cys | Phe | Gly | Ser | Ser | Asp |
|     |     | 35  |     |     |     |     | 40  |     |     |     |     | 45  |     |     |     |
| Ser | Met | Gly | His | Lys | Leu | Arg | Ile | Arg | Thr | Pro | Ser | Ala | Thr | Thr | Arg |
|     | 50  |     |     |     |     | 55  |     |     |     |     | 60  |     |     |     |     |
| Arg | Leu | Thr | Lys | Asp | Phe | Asn | Pro | Leu | Lys | Val | Val | Cys | Ile | Asp | Tyr |
| 65  |     |     |     |     | 70  |     |     |     |     | 75  |     |     |     |     | 80  |
| Pro | Arg | Pro | Glu | Leu | Asp | Asn | Thr | Val | Asn | Tyr | Leu | Glu | Ala | Ala | Leu |
|     |     |     |     | 85  |     |     |     |     | 90  |     |     |     |     | 95  |     |

```
Leu  Ser  Ser  Ser  Phe  Arg  Thr  Ser  Ser  Arg  Pro  Thr  Lys  Pro  Leu  Glu
               100                 105                      110

Ile  Val  Ile  Ala  Gly  Ala  Gly  Leu  Gly  Gly  Leu  Ser  Thr  Ala  Lys  Tyr
               115                 120                      125

Leu  Ala  Asp  Ala  Gly  His  Lys  Pro  Ile  Leu  Leu  Glu  Ala  Arg  Asp  Val
          130                      135                      140

Leu  Gly  Gly  Lys  Val  Ala  Ala  Trp  Lys  Asp  Asp  Gly  Asp  Trp  Tyr
145                      150                 155                      160

Glu  Thr  Gly  Leu  His  Ile  Phe  Phe  Gly  Ala  Tyr  Pro  Asn  Met  Gln  Asn
                    165                 170                      175

Leu  Phe  Gly  Glu  Leu  Gly  Ile  Asn  Asp  Arg  Leu  Gln  Trp  Lys  Glu  His
               180                      185                 190

Ser  Met  Ile  Phe  Ala  Met  Pro  Asn  Lys  Pro  Gly  Glu  Phe  Ser  Arg  Phe
               195                 200                      205

Asp  Phe  Pro  Glu  Ala  Leu  Pro  Ala  Pro  Leu  Asn  Gly  Thr  Leu  Ala  Ile
     210                      215                      220

Leu  Lys  Asn  Asn  Glu  Met  Leu  Thr  Trp  Pro  Glu  Lys  Val  Lys  Phe  Ala
225                           230                 235                      240

Ile  Gly  Leu  Leu  Pro  Ala  Met  Leu  Gly  Gly  Gln  Ser  Tyr  Val  Glu  Ala
               245                      250                      255

Gln  Asp  Gly  Leu  Ser  Val  Lys  Asp  Trp  Met  Arg  Lys  Gln  Gly  Val  Pro
               260                      265                      270

Asp  Arg  Val  Thr  Asp  Lys  Val  Phe  Ile  Ala  Met  Ser  Lys  Ala  Leu  Asn
          275                      280                      285

Phe  Ile  Asn  Pro  Asp  Glu  Leu  Ser  Met  Gln  Cys  Ile  Leu  Ile  Ala  Leu
     290                      295                 300

Asn  Arg  Phe  Leu  Gln  Glu  Lys  His  Gly  Ser  Lys  Met  Ala  Phe  Leu  Asp
305                      310                 315                      320

Gly  Asn  Pro  Pro  Glu  Arg  Leu  Cys  Met  Pro  Ile  Val  Glu  His  Ile  Glu
                    325                 330                      335

Ser  Lys  Gly  Gly  Gln  Val  Arg  Leu  Asn  Ser  Arg  Ile  Lys  Lys  Ile  Glu
               340                      345                 350

Leu  Asn  Glu  Asp  Gly  Ser  Val  Lys  Cys  Phe  Ile  Leu  Asn  Asn  Gly  Ser
          355                      360                      365

Thr  Ile  Lys  Gly  Asp  Ala  Phe  Val  Phe  Ala  Thr  Pro  Val  Asp  Ile  Phe
     370                      375                 380

Lys  Leu  Leu  Leu  Pro  Glu  Asp  Trp  Lys  Glu  Ile  Pro  Tyr  Phe  Gln  Lys
385                      390                 395                      400

Leu  Glu  Lys  Leu  Val  Gly  Val  Pro  Val  Ile  Asn  Val  His  Ile  Trp  Phe
               405                 410                      415

Asp  Arg  Lys  Leu  Lys  Asn  Thr  Ser  Asp  Asn  Leu  Leu  Phe  Ser  Arg  Ser
               420                 425                      430

Pro  Leu  Leu  Ser  Val  Tyr  Ala  Asp  Met  Ser  Val  Thr  Cys  Lys  Glu  Tyr
               435                 440                      445

Tyr  Asn  Pro  Asn  Gln  Ser  Met  Leu  Glu  Leu  Val  Phe  Ala  Pro  Ala  Glu
     450                      455                 460

Glu  Trp  Ile  Asn  Arg  Ser  Asp  Ser  Glu  Ile  Ile  Asp  Ala  Thr  Met  Lys
465                      470                 475                      480

Glu  Leu  Ala  Lys  Leu  Phe  Pro  Asp  Glu  Ile  Ser  Ala  Asp  Gln  Ser  Lys
               485                      490                 495

Ala  Lys  Ile  Leu  Lys  Tyr  His  Val  Val  Lys  Thr  Pro  Arg  Ser  Val  Tyr
               500                      505                      510

Lys  Thr  Val  Pro  Gly  Cys  Glu  Leu  Cys  Arg  Pro  Leu  Gln  Arg  Ser  Pro
               515                 520                      525
```

Ile Glu Gly Phe Tyr Leu Ala Gly Asp Tyr Thr Lys Gln Lys Tyr Leu
    530                 535                 540

Ala Ser Met Glu Gly Ala Val Leu Ser Gly Lys Leu Cys Ala Gln Ala
545                 550                 555                 560

Ile Val Gln Asp Tyr Glu Leu Leu Leu Gly Arg Ser Gln Lys Lys Leu
                565                 570                 575

Ala Glu Ala Ser Val Val
            580

( 2 ) INFORMATION FOR SEQ ID NO:7:

( i ) SEQUENCE CHARACTERISTICS:
        ( A ) LENGTH: 2308 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 396..2141

( x i ) SEQUENCE DESCRIPTION: SEQ ID NO:7:

```
AGCCAAACAT AAAGGCCGGT CCAGTGCGAG TTACTGCAAA TTGAGTTTGG AGTGAGGATT        60

AAAGGAAGAT AACATATTTC CAGCTAAATA GCAAACAAAT GACCCATTAA CGGAAGTGGC       120

CAAACCACCA AATTCAGGCA TCTCCACCAA ATATTAGTTT TTTATACACA AAGATTCAG        180

CATTCTTTAT CAGGGGTATC TTTTTGTGGG TAACTGCCAA ACCACCACAA ATTTTCAGTT       240

CCCACTCTTA ACTCTTTCAA CTTCAACACA ACAACTTATT TGCTTTTCCT TCTTTGCTTA       300

TCTTGTGCAT AACGATTTCC TACAACTTTA GCATAATCTT GGTTTGTAAT CCACAACGTG       360

AAACACAACT CCTAGGCGGT TTCATACCGA GTAAA ATG CCC CAA ATT GGA CTT          413
                                       Met Pro Gln Ile Gly Leu
                                         1               5
```

GTT TCT GCC GTT AAT TTG AGA GTC CAA GGT AAT TCA GCT TAT CTT TGG       461
Val Ser Ala Val Asn Leu Arg Val Gln Gly Asn Ser Ala Tyr Leu Trp
         10                  15                  20

AGC TCG AGG TCT TCT TTG GGA ACT GAA AGT CAA GAT GGT CAC TTG CAA       509
Ser Ser Arg Ser Ser Leu Gly Thr Glu Ser Gln Asp Gly His Leu Gln
     25                  30                  35

AGG AAT TTG TTA TGT TTT GGT AGT AGC GAC TCC ATG GGG CAT AAG TTA       557
Arg Asn Leu Leu Cys Phe Gly Ser Ser Asp Ser Met Gly His Lys Leu
 40                  45                  50

AGG ATT CGT ACT CCA AGT GCC ATG ACC AGA AGA TTG ACA AAG GAC TTT       605
Arg Ile Arg Thr Pro Ser Ala Met Thr Arg Arg Leu Thr Lys Asp Phe
 55                  60                  65                  70

AAT CCT TTA AAG GTA GTC TGC ATT GAT TAT CCA AGA CCA GAG CTA GAC       653
Asn Pro Leu Lys Val Val Cys Ile Asp Tyr Pro Arg Pro Glu Leu Asp
                 75                  80                  85

AAT ACA GTT AAC TAT TTG GAG GCG GCG TTA TTA TCA TCA TCA TTT CGT       701
Asn Thr Val Asn Tyr Leu Glu Ala Ala Leu Leu Ser Ser Ser Phe Arg
             90                  95                 100

ACT TCC TCA CGC CCA ACT AAA CCA TTG GAG ATT GTT ATT GCT GGT GCA       749
Thr Ser Ser Arg Pro Thr Lys Pro Leu Glu Ile Val Ile Ala Gly Ala
         105                 110                 115

GGT TTG GGT GGT TTG TCT ACA GCA AAA TAT CTG GCA GAT GCT GGT CAC       797
Gly Leu Gly Gly Leu Ser Thr Ala Lys Tyr Leu Ala Asp Ala Gly His
     120                 125                 130

AAA CCG ATA TTG CTG GAG GCA AGA GAT GTC CTA GGT GGA AAG GTA GCT       845
Lys Pro Ile Leu Leu Glu Ala Arg Asp Val Leu Gly Gly Lys Val Ala

-continued

| | | | | | | | | | | | | | | | | |
|---|---|---|---|---|---|---|---|---|---|---|---|---|---|---|---|---|
| 135 | | | | | 140 | | | | | 145 | | | | | 150 | |

GCA TGG AAA GAT GAT GAT GGA GAT TGG TAT GAG ACT GGG TTG CAC ATA    893
Ala Trp Lys Asp Asp Asp Gly Asp Trp Tyr Glu Thr Gly Leu His Ile
            155             160                 165

TTC TTT GGG GCT TAC CCA AAT ATG CAG AAC TTG TTT GGA GAA CTA GGG    941
Phe Phe Gly Ala Tyr Pro Asn Met Gln Asn Leu Phe Gly Glu Leu Gly
        170                 175                 180

ATA AAC GAT CGG TTG CAG TGG AAG GAA CAT TCA ATG ATA TTT GCG ATG    989
Ile Asn Asp Arg Leu Gln Trp Lys Glu His Ser Met Ile Phe Ala Met
        185                 190                 195

CCT AAC AAG CCA GGG GAG TTC AGC CGC TTT GAT TTT CCT GGA GCT CTT   1037
Pro Asn Lys Pro Gly Glu Phe Ser Arg Phe Asp Phe Pro Gly Ala Leu
    200                 205                 210

CCT GCG CCA TTA AAT GGA ATT TTG GCC ATA CTA AAG AAC AAC GAA ATG   1085
Pro Ala Pro Leu Asn Gly Ile Leu Ala Ile Leu Lys Asn Asn Glu Met
215                 220                 225                 230

CTT ACG TGG CCC GAA AAA GTC AAA TTT GCT ATT GGA CTC TTG CCA GCA   1133
Leu Thr Trp Pro Glu Lys Val Lys Phe Ala Ile Gly Leu Leu Pro Ala
                235                 240                 245

ATG CTT GGA GGG CAA TCT TAT GTT GAA GCT CAA GAC GGT TTA AGT GTT   1181
Met Leu Gly Gly Gln Ser Tyr Val Glu Ala Gln Asp Gly Leu Ser Val
        250                 255                 260

AAG GAC TGG ATG AGA AAG CAA GGT GTG CCT GAT AGG GTG ACA GAT GAG   1229
Lys Asp Trp Met Arg Lys Gln Gly Val Pro Asp Arg Val Thr Asp Glu
        265                 270                 275

GTG TTC ATT GCC ATG TCA AAG GCA CTT AAC TTC ATA AAC CCT GAC GAG   1277
Val Phe Ile Ala Met Ser Lys Ala Leu Asn Phe Ile Asn Pro Asp Glu
        280                 285                 290

CTT TCG ATG CAG TGC ATT TTG ATT GCT TTG AAC AGA TTT CTT CAG GAG   1325
Leu Ser Met Gln Cys Ile Leu Ile Ala Leu Asn Arg Phe Leu Gln Glu
295                 300                 305                 310

AAA CAT GGT TCA AAA ATG GCC TTT TTA GAT GGT AAC CCT CCT GAG AGA   1373
Lys His Gly Ser Lys Met Ala Phe Leu Asp Gly Asn Pro Pro Glu Arg
                315                 320                 325

CTT TGC ATG CCG ATT GTT GGA CAT ATT GAG TCA AAA GGT GGC CAA GTC   1421
Leu Cys Met Pro Ile Val Gly His Ile Glu Ser Lys Gly Gly Gln Val
            330                 335                 340

AGA CTA AAC TCA CGA ATA AAA AAG AAT GAG CTG AAT GAG GAT GGA AGT   1469
Arg Leu Asn Ser Arg Ile Lys Lys Asn Glu Leu Asn Glu Asp Gly Ser
        345                 350                 355

GTC AAA TGT TTT ATA CTG AAT AAT GGC AGT ACA ATT AAA GGA GAT GCT   1517
Val Lys Cys Phe Ile Leu Asn Asn Gly Ser Thr Ile Lys Gly Asp Ala
        360                 365                 370

ATT GTG TTT GCC ACT CCA GTG GAT ATC TTC AAG CCT CTT TTG CCT GAA   1565
Ile Val Phe Ala Thr Pro Val Asp Ile Phe Lys Pro Leu Leu Pro Glu
375                 380                 385                 390

GAG TGG AAA GAG ATC CCA TAT TTC CAA AAG TTG GAG AAG CTA GTG GGA   1613
Glu Trp Lys Glu Ile Pro Tyr Phe Gln Lys Leu Glu Lys Leu Val Gly
                395                 400                 405

GTT CCT GTG ATA AAT GTC CAT ATA TGG TTT GAC AGA AAA CTG AAG AAC   1661
Val Pro Val Ile Asn Val His Ile Trp Phe Asp Arg Lys Leu Lys Asn
            410                 415                 420

ACA TCT GAT AAT CTG CTC TTC AGC AGA AGC CCG TTG CTC AGT GTG TAT   1709
Thr Ser Asp Asn Leu Leu Phe Ser Arg Ser Pro Leu Leu Ser Val Tyr
        425                 430                 435

GCT GAC ATG TCT GTT ACA TGT AAG GAA TAT TAC CAC TCC AAT CAG TCT   1757
Ala Asp Met Ser Val Thr Cys Lys Glu Tyr Tyr His Ser Asn Gln Ser
        440                 445                 450

ATG TTG GAA TTG GTA TTT GCA CCT GCA GAA GAG TGG ATA AAT CGT AGT   1805
Met Leu Glu Leu Val Phe Ala Pro Ala Glu Glu Trp Ile Asn Arg Ser

| | | | | | | | | | | | | | | | | |
|---|---|---|---|---|---|---|---|---|---|---|---|---|---|---|---|---|
|455| | | | |460| | | |465| | | |470| | | |
|GAC|TCA|GAA|ATT|ATT|GAT|GCT|ACA|ATG|AAG|GAA|CTA|GCA|AAG|CTT|TTC|1853|
|Asp|Ser|Glu|Ile|Ile 475|Asp|Ala|Thr|Met|Lys 480|Glu|Leu|Ala|Lys|Leu 485|Phe| |
|CCT|GAC|GAA|ATT|TCG|GCA|GAT|CAG|AGC|AAA|GCA|AAA|ATA|TTG|AAG|TAT|1901|
|Pro|Asp|Glu|Ile 490|Ser|Ala|Asp|Gln|Ser 495|Lys|Ala|Lys|Ile|Leu 500|Lys|Tyr| |
|CAC|ATT|GTC|AAA|ACT|CCA|AGG|TCT|GTT|TAT|AAA|ACT|GTG|CCA|GGT|TGT|1949|
|His|Ile|Val 505|Lys|Thr|Pro|Arg|Ser|Val 510|Tyr|Lys|Thr|Val 515|Pro|Gly|Cys| |
|GAA|CCC|TGT|CGG|CCC|TTG|CAA|AGA|CCT|CCT|ATT|GAG|GGG|TTT|TAT|TTA|1997|
|Glu|Pro 520|Cys|Arg|Pro|Leu|Gln 525|Arg|Pro|Pro|Ile|Glu 530|Gly|Phe|Tyr|Leu| |
|GCT|GGT|GAC|TAC|ACG|AAA|CAG|AAA|TAC|TTG|GCT|TCA|ATG|GAA|GGT|GCT|2045|
|Ala 535|Gly|Asp|Tyr|Thr|Lys 540|Gln|Lys|Tyr|Leu|Ala 545|Ser|Met|Glu|Gly|Ala 550| |
|GTC|TTA|TCA|GGA|AAG|CTT|TGT|GCC|CAA|GCT|ATT|GTA|CAG|GAT|TAC|GAG|2093|
|Val|Leu|Ser|Gly|Lys 555|Leu|Cys|Ala|Gln|Ala 560|Ile|Val|Gln|Asp|Tyr 565|Glu| |
|TTA|CTT|CTT|GGA|CGG|AGC|CAG|AAG|AAG|TTG|GCA|GAA|GCA|AGC|GTA|GTT|2141|
|Leu|Leu|Leu|Gly 570|Arg|Ser|Gln|Lys|Lys 575|Leu|Ala|Glu|Ala|Ser 580|Val|Val| |

```
TAGCATGGTG  AACTAAAATG  TTGCTTCTGT  ACACTAAATT  TAAGATGAAG  GCGGCCACAC   2201

TGAATTAGCG  TTGTACACAA  CATATACAAG  GACAGTACAA  CATTGACCCC  AAATACGAGA   2261

AATGTTACAC  AAATATGAAA  TATGTGCTCT  GCTTTCCCTC  CAAAACC                  2308
```

( 2 ) INFORMATION FOR SEQ ID NO:8:

( i ) SEQUENCE CHARACTERISTICS:
        ( A ) LENGTH: 582 amino acids
        ( B ) TYPE: amino acid
        ( D ) TOPOLOGY: linear ( i i ) MOLECULE TYPE: protein ( x i ) SEQUENCE DESCRIPTION: SEQ ID NO:8:

| | | | | | | | | | | | | | | | |
|---|---|---|---|---|---|---|---|---|---|---|---|---|---|---|---|
|Met 1|Pro|Gln|Ile|Gly 5|Leu|Val|Ser|Ala|Val 10|Asn|Leu|Arg|Val|Gln 15|Gly|
|Asn|Ser|Ala|Tyr 20|Leu|Trp|Ser|Ser|Arg 25|Ser|Ser|Leu|Gly|Thr 30|Glu|Ser|
|Gln|Asp|Gly 35|His|Leu|Gln|Arg|Asn 40|Leu|Leu|Cys|Phe|Gly 45|Ser|Ser|Asp|
|Ser|Met 50|Gly|His|Lys|Leu|Arg 55|Ile|Arg|Thr|Pro|Ser 60|Ala|Met|Thr|Arg|
|Arg 65|Leu|Thr|Lys|Asp|Phe 70|Asn|Pro|Leu|Lys|Val 75|Val|Cys|Ile|Asp|Tyr 80|
|Pro|Arg|Pro|Glu|Leu 85|Asp|Asn|Thr|Val|Asn 90|Tyr|Leu|Glu|Ala|Ala 95|Leu|
|Leu|Ser|Ser|Ser|Phe 100|Arg|Thr|Ser|Ser|Arg 105|Pro|Thr|Lys|Pro|Leu 110|Glu|
|Ile|Val|Ile|Ala|Gly 115|Ala|Gly|Leu|Gly 120|Gly|Leu|Ser|Thr|Ala 125|Lys|Tyr|
|Leu|Ala|Asp 130|Ala|Gly|His|Lys 135|Pro|Ile|Leu|Leu|Glu 140|Ala|Arg|Asp|Val|
|Leu|Gly 145|Gly|Lys|Val|Ala|Ala 150|Trp|Lys|Asp|Asp|Gly 155|Asp|Trp|Tyr 160|
|Glu|Thr|Gly|Leu|His 165|Ile|Phe|Phe|Gly|Ala 170|Tyr|Pro|Asn|Met|Gln 175|Asn|

```
Leu  Phe  Gly  Glu  Leu  Gly  Ile  Asn  Asp  Arg  Leu  Gln  Trp  Lys  Glu  His
               180                 185                      190

Ser  Met  Ile  Phe  Ala  Met  Pro  Asn  Lys  Pro  Gly  Glu  Phe  Ser  Arg  Phe
          195                 200                      205

Asp  Phe  Pro  Gly  Ala  Leu  Pro  Ala  Pro  Leu  Asn  Gly  Ile  Leu  Ala  Ile
     210                 215                      220

Leu  Lys  Asn  Asn  Glu  Met  Leu  Thr  Trp  Pro  Glu  Lys  Val  Lys  Phe  Ala
225                      230                 235                           240

Ile  Gly  Leu  Leu  Pro  Ala  Met  Leu  Gly  Gly  Gln  Ser  Tyr  Val  Glu  Ala
               245                      250                      255

Gln  Asp  Gly  Leu  Ser  Val  Lys  Asp  Trp  Met  Arg  Lys  Gln  Gly  Val  Pro
               260                 265                      270

Asp  Arg  Val  Thr  Asp  Glu  Val  Phe  Ile  Ala  Met  Ser  Lys  Ala  Leu  Asn
          275                 280                 285

Phe  Ile  Asn  Pro  Asp  Glu  Leu  Ser  Met  Gln  Cys  Ile  Leu  Ile  Ala  Leu
     290                 295                      300

Asn  Arg  Phe  Leu  Gln  Glu  Lys  His  Gly  Ser  Lys  Met  Ala  Phe  Leu  Asp
305                      310                 315                           320

Gly  Asn  Pro  Pro  Glu  Arg  Leu  Cys  Met  Pro  Ile  Val  Gly  His  Ile  Glu
               325                 330                      335

Ser  Lys  Gly  Gly  Gln  Val  Arg  Leu  Asn  Ser  Arg  Ile  Lys  Lys  Asn  Glu
               340                 345                      350

Leu  Asn  Glu  Asp  Gly  Ser  Val  Lys  Cys  Phe  Ile  Leu  Asn  Asn  Gly  Ser
          355                 360                      365

Thr  Ile  Lys  Gly  Asp  Ala  Ile  Val  Phe  Ala  Thr  Pro  Val  Asp  Ile  Phe
     370                 375                      380

Lys  Pro  Leu  Leu  Pro  Glu  Glu  Trp  Lys  Glu  Ile  Pro  Tyr  Phe  Gln  Lys
385                      390                 395                           400

Leu  Glu  Lys  Leu  Val  Gly  Val  Pro  Val  Ile  Asn  Val  His  Ile  Trp  Phe
               405                 410                      415

Asp  Arg  Lys  Leu  Lys  Asn  Thr  Ser  Asp  Asn  Leu  Leu  Phe  Ser  Arg  Ser
               420                 425                      430

Pro  Leu  Leu  Ser  Val  Tyr  Ala  Asp  Met  Ser  Val  Thr  Cys  Lys  Glu  Tyr
          435                 440                      445

Tyr  His  Ser  Asn  Gln  Ser  Met  Leu  Glu  Leu  Val  Phe  Ala  Pro  Ala  Glu
     450                 455                      460

Glu  Trp  Ile  Asn  Arg  Ser  Asp  Ser  Glu  Ile  Ile  Asp  Ala  Thr  Met  Lys
465                      470                 475                           480

Glu  Leu  Ala  Lys  Leu  Phe  Pro  Asp  Glu  Ile  Ser  Ala  Asp  Gln  Ser  Lys
               485                 490                      495

Ala  Lys  Ile  Leu  Lys  Tyr  His  Ile  Val  Lys  Thr  Pro  Arg  Ser  Val  Tyr
               500                 505                      510

Lys  Thr  Val  Pro  Gly  Cys  Glu  Pro  Cys  Arg  Pro  Leu  Gln  Arg  Pro  Pro
          515                 520                      525

Ile  Glu  Gly  Phe  Tyr  Leu  Ala  Gly  Asp  Tyr  Thr  Lys  Gln  Lys  Tyr  Leu
     530                 535                      540

Ala  Ser  Met  Glu  Gly  Ala  Val  Leu  Ser  Gly  Lys  Leu  Cys  Ala  Gln  Ala
545                      550                 555                           560

Ile  Val  Gln  Asp  Tyr  Glu  Leu  Leu  Leu  Gly  Arg  Ser  Gln  Lys  Lys  Leu
               565                 570                      575

Ala  Glu  Ala  Ser  Val  Val
               580
```

DNA SEQUENCES ENCODING ENZYMES USEFUL IN CAROTENOID BIOSYNTHESIS

BACKGROUND OF THE INVENTION

The present invention relates to genetic engineering, and in particular to nucleotide sequences encoding enzymes for catalyzing the biosynthesis of carotenoids, such as zeta-carotene.

Carotenoids are 40-carbon terpenoids having eight connected isoprene units. Carotenoids include phytoene, zeta-carotene, lycopene, beta-carotene, zeaxanthin and zeaxanthin diglucoside. See Krinsky et al., *Carotenoids: Chemistry and Biology*, Plenum Press, pp. 279-291 (1990) and Nes et al., *Regulation of Isopentenoid Metabolism*, ACS Sym. Ser. 497 (1992). A biosynthetic pathway for the various carotenoids is set forth in European Patent Application No. 393,690, U.S. Pat. No. 5,304,478 and PCT WO 91/13078, which are incorporated herein by reference.

Certain carotenoids can be considered intermediates in the biosynthetic pathway of other carotenoids. However, carotenoids such as phytoene have been found to have a useful application in absorbing ultraviolet radiation. See U.S. Pat. No. 4,642,318. Furthermore, the carotenoid lycopene, has been found to have use as a coloring agent in situations in which a red color is desired. See Taylor, *Carotenoids: Products, Applications and Markets*, Decision Resources, Inc. (1990). Other biosynthetically produced carotenoids have found use as coloring agents, particularly for foods, in situations in which an orange or yellow color is desired. Carotenoids also have been found to be useful as animal feeds, as well as in the pharmaceutical and cosmetics industries. See Taylor, *Carotenoids: Products, Applications and Markets*, Decision Resources, Inc. (1990), and E-Siong Tee, *Crit. Rev. Food Sci and Nutri.*, Vol. 31, p.103 (1992).

It would be highly desirable to have the capability of altering the biosynthetic pathway for carotenoids, particularly in higher plants such as the solanaceae. As such, it would be desirable to provide nucleotide sequences that encode enzymes useful in the carotenoid biosynthesis pathway, such as phytoene desaturase. In particular, it would be desirable to provide the nucleotide sequences that encode phytoene desaturase from a higher plant species, such as a Nicotiana species.

SUMMARY OF THE INVENTION

The present invention relates to nucleotide sequences (e.g.,DNA and RNA) capable of encoding a polypeptide which has enzymatic activity for producing a carotenoid (e.g., zeta-carotene). Such a polypeptide is referred to as phytoene desaturase. The DNA is isolated from a Nicotiana species, such as *Nicotiana benthamiana* or *Nicotiana tabacum*. The nucleotide sequences encode the enzyme phytoene desaturase, and variants of those sequences encoding enzymes exhibiting the same biological activity as phytoene desaturase. The nucleotide sequences correspond to, or substantially to, those DNA sequences specified in SEQ ID NOS: 1, 3, 5 and 7. The nucleotide sequences may be provided as DNA or RNA in an isolated, substantially pure form.

In another aspect, the present invention relates to certain polypeptides which may be provided in a purified (e.g., isolated and substantially pure) form. The polypeptides have enzymatic activity for producing zeta-carotene. Those polypeptides are encoded by nucleotide sequences which correspond to, or substantially to, those sequences specified SEQ ID NOS: 1, 3, 5 and 7. Those polypeptides have amino acid sequences which correspond to, or substantially to, those amino acid sequences specified in SEQ ID NOS: 2, 4, 6 and 8, respectively. Polypeptides having amino acid sequences which correspond substantially to those encoded by the specified sequences have different amino acid sequences (e.g., a minor number of amino acids of the sequence can be deleted, added or substituted), but the same type of biological activities as those encoded by the specified sequences, although those biological activities may differ in degree. In another aspect, the present invention relates to fragments of polypeptides (e.g., polypeptide derivatives) encoded by nucleotide sequences which correspond to, or substantially to, certain nucleotide subsequences contained within those sequences specified in SEQ ID NOS: 1, 3, 5 and 7. Such fragments represent domains of the full length (i.e., intact) polypeptides. Such fragments can be, for example, transit peptides useful for directing polypeptides to subcellular compartments, or polypeptide domains having properties such as catalytic activity, substrate binding activity, and the like.

Any of the nucleotide sequences of the present invention can be incorporated (i.e., in an operative fashion) into heterologous systems (e.g., yeast, bacteria or certain plants) in order that the respective polypeptides can be synthesized thereby. The nucleotide sequences can be incorporated into plants (e.g., rice, corn, tobacco or tomato), using transformation techniques or viral gene expression systems. The RNA molecules or polypeptides encoded by those nucleotide sequences can be used to alter the biosynthetic pathway of carotenoids and related compounds, or the polypeptides can be isolated in order to be used as enzymes in the in vitro synthesis of carotenoids.

In another aspect, the present invention relates to recombinant DNA or RNA molecules. Such molecules include DNA sequences, corresponding RNA sequences, or subsequences of such DNA and RNA sequences. Such sequences and subsequences (e.g., promoters, enhancers, terminators and replication signals) are capable of facilitating the expression of RNA molecules or enzymes useful for altering carotenoid biosynthesis. These DNA sequences or subsequences have nucleotide sequences which include, or substantially include, at least one of those sequences specified in SEQ ID NOS: 1, 3, 5 and 7. These DNA sequences may be obtained or isolated from a Nicotiana species, or may originate from unrelated organisms. The recombinant molecule can be considered a plasmid or a vector. The recombinant molecule can be a plasmid or vector tailored for transfer of the recombinant molecule to plant or other cells. Recombinant molecules also can be contained in a transgenic plant cell, such as a tobacco plant cell.

In another aspect, the invention relates to the delivery and expression of sequences or subsequences as described in SEQ ID NOS: 1, 3, 5 and 7 via transient virus-based gene delivery systems. Such a system is described in European Patent Application No. 406,267 and U.S. Pat. No. 5,316,931, which are incorporated herein by reference. Such a system involves delivery of a selected nucleotide sequence as part of, or in conjunction with, a self-replicating DNA or RNA molecule (e.g., a virus), such that the exogenous gene is replicated and expressed during the course of replication and expression of viral or virus-based nucleic acids and proteins. Such gene delivery systems may be used for expression of nucleic acid sequences or subsequences as described in SEQ ID NOS: 1, 3, 5 and 7 in either sense orientation for the expression of polypeptides, or in antisense orientation for the delivery of RNA molecules capable of inhibiting expression of the target gene or other homologous genes. Genes or gene sequences delivered in such a manner are considered to be functionally inserted in the target organism such as a tobacco plant.

A further aspect of the present invention is a crop composed of a plurality of plants having the nucleotide sequences of the present invention functionally inserted therein, and planted together in an agricultural field, including a greenhouse.

Compositions including genetic sequences and subsequences encoding carotenoid enzymes for expression in plants, such as tobacco plants, impart those plants with the ability to produce altered levels of carotenoids. As such, there is provided a method for altering the synthesis of carotenoids in plants, which method involves inserting a recombinant genetic construct into plant cells. Such a construct can provide for synthesis of naturally occurring carotenoids within such plant cells. For example, certain recombinant genetic constructs of the present invention are capable of expressing at least one naturally occurring enzyme in order that resulting transformed plants exhibit enhanced ability to produce carotenoids. As such, there is provided a method for altering the synthetic pathway of carotenoids in plants.

In yet another aspect, the present invention relates to antisense sequences for those sequences which correspond to, or substantially to, the totality or a subset of those nucleic acid sequences specified in SEQ ID NOS: 1, 3, 5 and 7. As such, those sequences encode RNA molecules capable of inhibiting expression of the corresponding and related genes. As such, the present invention provides for a method for altering the synthetic pathway of carotenoids. For example, the expression of an antisense molecule may be useful for preventing synthesis of a particular carotenoid. Alternatively, expression of an antisense molecule may be useful in accumulating relatively high levels of certain molecules upstream of a particular metabolic block. Another example is the use of such antisense molecules to deliberately direct metabolites toward one branch of a branched pathway.

DETAILED DESCRIPTION OF THE PREFERRED EMBODIMENTS

Figure 1:
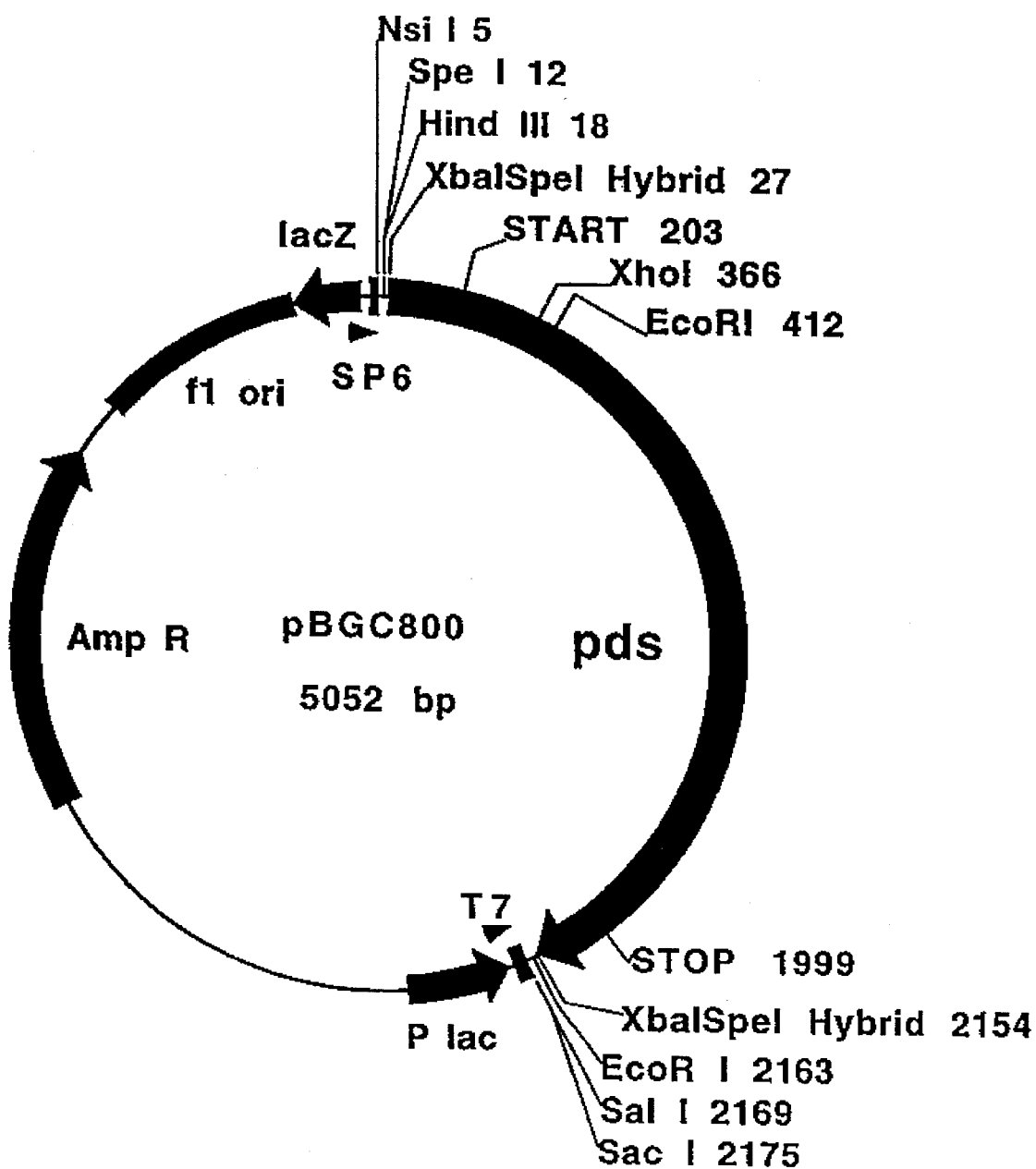
FIG. 1 is a map of the plasmid pBGC800 which contains the *Nicotiana benthamiana* phytoene desaturase allele 1 sequence as an SpeI fragment cloned into the XbaI site of commercially available pGEM9Zf(-) (Promega Corp., Madison, Wis.).

The nucleotide sequences of genetic materials of the present invention are endogenous to a Nicotiana species and are isolated from Nicotiana species. Most preferably, the nucleotide sequences are isolated from *Nicotiana benthamiana* or *Nicotiana tabacum*. Examples of other Nicotiana species include *Nicotiana debneyi, Nicotiana glauca, Nicotiana glutinosa, Nicotiana rustica,* and *Nicotiana svaveolens*. Examples of cultivars of *Nicotiana tabacum* include flue-cured tobacco (e.g., NK 326), Burley tobacco (e.g., KY 14) and Maryland tobacco (e.g., MD 609).

The nucleotide sequence of isolated genetic material of the present invention can be obtained by a variety of techniques. The sequence can be obtained by sequencing non-vector nucleotide sequences of recombinant molecules. Nucleotide sequence information can be obtained by employing widely used DNA sequencing protocols, such as Maxam and Gilbert sequencing, dideoxy nucleotide sequencing, and the like. Examples of suitable nucleotide sequencing protocols can be found in Berger and Kimmel, *Methods in Enzymology* Vol. 51, *Guide to Molecular Cloning Techniques,* Academic Press (1987). Nucleotide sequence information from several recombinant DNA isolates, including isolates from both cDNA and genomic libraries, can be combined so as to provide the entire amino acid coding sequence, as well as the nucleotide sequences of upstream and downstream nucleotide sequences.

For gene isolation, mRNA is converted into cDNA, and the resulting cDNA is cloned. The cloned cDNA then can be used directly, or it, or sequences derived from it, can be utilized for acquiring the entire gene, either (i) from a library (e.g., in a lambda or plasmid vector) using sequence information to screen the library and detect the desired clone, or (ii) by amplification with PCR (i.e., polymerase chain reaction) and subsequent cloning into a suitable vector. For example, the 5' and 3' RACE (Rapid Amplification of cDNA Ends) reactions can be used to clone overlapping 5' and 3' ends of the gene of interest with subsequent assembly of the complete gene.

Nucleotide sequences obtained from sequencing specific genetic library isolates can be subjected to further analysis in order to identify regions of interest in the genetic material. These regions of interest include additional open reading frames, promoter sequences, termination sequences, and the like. Isolated DNA can be characterized as being selected from the group consisting of:

(a) Isolated DNA selected from the group consisting of DNA having the nucleotide sequence which corresponds to, or substantially to, sequences described in SEQ ID NOS: 1, 3, 5 and 7.

(b) Isolated DNA which hybridizes to isolated DNA of (a) above which encodes an enzyme or fragment thereof having carotenoid biosynthetic activity. Hybridization of such sequences may, for example, be carried out under stringent conditions (e.g., conditions represented by a wash stringency of 0.03M NaCl, 0.003M sodium citrate, 0.1% SDS at 70° C. to DNA of (a) above) in a standard in situ hybridization assay. See J. Sambrook et al., *Molecular Cloning: A Laboratory Manual (2d Ed.)*, Cold Spring Harbor Laboratory, Cold Spring Harbor, N.Y. (1989). In general, such sequences will be at least 95% homologous, often at least 98% homologous, and even at least 99% homologous with the sequences of (a) above. (c) Isolated DNA homologous to isolated DNA of (a) and (b) above. Homology relates to substantial or complete identity of nucleic acid sequences; and two nucleic acid fragments are homologous if they are capable of hybridizing to one another under hybridization conditions described in Maniatis et al., *Molecular Cloning: A Laboratory Manual,* Cold Spring Harbor Laboratory, Cold Spring Harbor, N.Y., pp. 324–325 (1982). Homologous sequences can be identified that contain less than about 5% base pair mismatches by using the following wash conditions: 2 x SSC, 0.1% SDS, room temperature twice, 30 minutes each; then 2 x SSC, room temperature twice, 10 minutes each. Homology can be assessed using computer programs such as DNASIS™ and PCGene (LKB, Hitachi Corporation, Japan, and Intelligenetics, Palo Alto, Calif.) whereby the degree of homology is within the limits of homology considered significant by Bost et al., *Biochem. Biophys. Res. Commun.,* Vol. 128, pp. 1373–1380 (1985). More preferably, homologous nucleic acid strands contain less than 2% base pair mismatches, even more preferably less than 1% base pair mismatches. These degrees of homology can be selected by using more stringent wash conditions for identification of clones from gene libraries (or other sources of genetic material), as is well known in the art.

(d) Isolated DNA differing from the isolated DNA of (a), (b) and (c) above in nucleotide sequence due to the degeneracy of the genetic code, and which encodes either (i) a polypeptide identical to the polypeptides described in SEQ ID NOS: 2, 4, 6 and 8, or (ii) an enzyme or fragment thereof having carotenoid biosynthetic activity.

The nucleotide sequences of the present invention are capable of encoding polypeptides having enzymatic activity for carotenoid biosynthesis. Such polypeptides have domains of amino acid sequences, including transit peptide regions and catalytic regions. The transit peptides which can be isolated are capable of directing proteins, or polypeptides which are fused to such transit peptides, to various subcellular locations (e.g., chloroplast membranes, chloroplast stroma and thylakoid membranes). The catalytic domains demonstrate enzymatic activity, can be isolated, and can be expressed in in vivo or in vitro systems.

A polypeptide derivative of a carotenoid biosynthetic enzyme can differ in length from the natural enzyme, but typically contains numerous amino acids from the natural enzyme in the same primary order as found in that enzyme as obtained from a natural source. Such a polypeptide molecule has substantially the same full length amino acid sequence as the natural enzyme but possesses minor amino acid substitutions that do not substantially affect the ability of that derivative to cause biosynthesis of carotenoids. Derivatives include glycosylated forms, aggregative conjugates with other enzyme molecules and covalent conjugates with unrelated chemical moieties. Covalent derivatives are prepared by linkage of functionalities to groups which are found in the enzyme amino acid chain or at the N- or C-terminal residue by means known in the art.

Isolated nucleotide sequences encoding biosynthetic enzymes can be used to produce purified enzymes or derivatives thereof by either recombinant DNA methodology or by in vitro polypeptide synthesis techniques. Purified and isolated polypeptides or nucleotide sequences are present in the substantial absence of other biological macromolecules of the same type. Purified genes and polypeptides of the present invention typically have at least 95% by weight, more preferably at least 99% by weight, and most preferably at least 99.8% by weight, of biological macromolecules of the same type present; but water, buffers, and other small molecules, especially molecules having a molecular weight of less than 1000, can be present.

Biosynthetic enzymes and polypeptide derivatives of those enzymes can be expressed by recombinant techniques when a DNA sequence encoding the relevant molecule is functionally inserted into a vector (e.g., in proper reading frame and orientation, as is well understood by those skilled in the art). Typically, the relevant gene will be inserted downstream from a promoter and will be followed by a stop codon, although production as a hybrid protein followed by cleavage may be used, if desired. In general, host-cell-specific sequences improving the production yield of enzyme and enzyme derivatives can be used, and appropriate control sequences (e.g., enhancer sequences, polyadenylation sequences, and ribosome binding sites) can be added to the expression vector.

A genetic construct can be prepared and used to transform plant cells. The transformed plant cells may be cells in culture, may be present as a disorganized mass in callus, leaf explants, or shoot cultures, or may be a post-transformation differentiated plant or plant part, such as seeds, leaves, roots, or the like. The foreign construct normally is present in all or substantially all of the cells of the plant tissue, but expression may be limited to particular cells or particular times in the development of the plant. The foreign construct normally includes transcriptional and translational initiation and termination signals, with the initiation signals 5' to the gene of interest and the termination signals 3' to the gene of interest.

The transcriptional initiation region which includes an RNA polymerase binding site (i.e., promoter) may be native to the host or may be derived from an alternative source, where the region is functional in the plant host. Other sources include the nos Agrobacterium T-DNA genes.

The transcriptional initiation regions may include, in addition to the RNA polymerase binding site, regions providing for regulation of transcription. The 3' termination region may be derived from the same gene as the transcriptional initiation region or from a different gene. For example, where the gene of interest has a transcriptional termination region functional in the host species, that region may be retained with the gene.

An example of an expression cassette is one that includes: a) the transcriptional initiation region, b) the biosynthetic enzyme gene under the transcriptional regulatory control of the transcription initiation region, c) the translation initiation codon, d) the coding sequence of the gene with or without introns, and e) the translational stop codons, followed by f) the transcriptional termination region. The transcriptional termination region includes the terminator, and may include a polyadenylation signal sequence and other sequences associated with transcriptional termination. The direction is 5' to 3' in the direction of transcription.

Where the expression product of the gene is to be located in a subcellular or extracellular compartment other than the cytoplasm, the gene usually is constructed to include particular amino acid sequences which result in translocation of the product to a particular site, which may be an organelle, such as the chloroplast, mitochondrion or nucleus, the cell plasma membrane, or may be secreted into the periplasmic space or into the external environment of the cell. Various secretory leaders, membrane integrator sequences, and translocation sequences for directing the peptide expression product to a particular site are described in the literature. See, for example, Cashmore et al., *Biotechnology*, Vol. 3, pp. 803–808 (1985), and Wickner and Lodish, *Science*, Vol. 230, pp. 400–407 (1985).

The expression cassette normally is carried on a vector having at least one replication system. For convenience, it is common to have a replication system function in *E. coli* such as ColE1, pSC101, pACYC184, or the like. In this manner, at each stage after each manipulation, the resulting construct may be cloned, sequenced, and the correctness of the manipulation determined.

In addition to the replication system, there frequently is at least one selectable marker present, which may be useful in one or more hosts, or different markers for individual hosts. That is, one marker may be employed for selection in a prokaryotic host, while another marker may be employed for selection in a eukaryotic host, particularly the plant species host. The markers may be protection against a biocide, such as antibiotics, toxins, heavy metals, or the like; or complementation, imparting prototropy to an auxotrophic host.

The various fragments comprising the various constructs, expression cassettes, markers, and the like may be introduced consecutively by restriction enzyme cleavage of an appropriate replication system, and insertion of the particular construct or fragment into the available sites. After ligation and cloning, the vector may be isolated for further manipulation. All of these techniques are amply exemplified in the literature and find particular exemplification in Sambrook et al., *Molecular Cloning: A Laboratory Manual second edition*, Cold Spring Harbor Laboratory, Cold Spring Harbor, N.Y., (1989).

Once the vector is completed, the vector may be introduced into plant cells. Techniques for transforming plant cells include microinjection, particle bombardment, direct DNA uptake, such as using polyethylene glycol, electroporation, viral infection, and transformation with Agrobacterium. See for example, D'Halluin et al., *The Plant Cell* vol. 4, pp. 1495–1505 (1992), Tomes et al., *Plant Mol. Biol.* vol. 14, pp. 261–268, Zhu et al., *Plant Cell, Tissue, and Organ Culture* vol. 22, pp. 135–145 for representative techniques.

The nucleotide sequence encoding a given polypeptide can also be functionally inserted into plants or transiently expressed by virus-based gene delivery systems. Such a system is described in European Patent Application Nos. 67,553, 194,809 and 406,267; PCT WO 93/20217 and U.S. Pat. Nos. 5,304,731 and 5,316,931; which are incorporated herein by reference. Such a system involves delivery of a selected nucleotide sequence as part of, or in conjunction with, a self-replicating DNA or RNA molecule (e.g., a virus), such that the exogenous gene is replicated and expressed during the course of replication and expression of viral or virus-based nucleic acids and proteins. Such gene delivery systems, in addition to enhancing effective gene "copy number" through the replicative potential of the given virus or virus-based nucleic acids, facilitate the timed delivery of such exogenous genes at the desired state of host development.

An exemplary virus-based gene delivery system employs tobacco mosaic virus. A DNA copy of the virus has a DNA sequence of the present invention inserted therein using conventional techniques of molecular cloning. The cloned DNA copy of the resulting viral vector then is transcribed to produce an RNA. The resulting RNA transcript vector then is used to inoculate a grown *Nicotiana benthamiana* plant by applying that RNA transcript onto a carborundum-dusted leaf of that plant and gently rubbing the treated area of the leaf in the direction of the leaf tip with a gloved finger. The plant so inoculated and infected with the virus vector is allowed to continue growing for about 3 weeks and then is harvested. The harvested plant can be extracted immediately or frozen for storage purposes. The leaf tissue so collected is mixed with a 10 mM phosphate buffer (pH 7.5) at a ratio of about 1:10 (w/v). The mixture is macerated using a high speed blender, and centrifuged so as to obtain a liquid inoculum. The inoculum then can be applied to a growing plant, such as a tobacco plant, by applying the inoculum to injured (e.g., lacerated) regions of that plant. For example, the upper most leaves of the growing plant can be cut using an inoculum-wetted cutting blade (e.g., by spray nozzles located in the cutting blade); or the inoculum can be sprayed onto a specific region of one leaf of the plant as a high pressure spray. The plant is allowed to continue growing in order that the viral vector can systemically infect the plant. At a desired stage of infection, the plant is harvested.

The following examples are provided in order to further illustrate the invention but should not be construed as limiting the scope thereof. Unless otherwise noted, all parts and percentages are by weight.

EXAMPLE 1

Isolation of genes encoding phytoene desaturase was carried out as follows:

Isolation of RNA from *Nicotiana benthamiana* and *Nicotiana tabacum*:

About 200 mg of plant leaf tissue was harvested and frozen in liquid nitrogen. The tissue was ground to a powder with a mortar and pestle and then transferred to a glass homogenizer. One ml of AGRIsol (Biogentex, Houston, Tex.) was added to the tissue, and the mixture was homogenized. The homogenate was transferred to a microfuge tube and 100 ul of chloroform was introduced into the tube. The mixture was shaken by hand for 20 sec. Then, the mixture was incubated for 5 min on ice, and centrifuged for 10 min at 10, 000 x g at 4° C. The aqueous phase of the centrifuged mixture was transferred to a separate tube, and the RNA was precipitated from that phase by addition of 1 volume of isopropanol. After incubation on ice for 5 min that sample was centrifuged for 10 min at 10, 000 x g at 4° C. The resulting pellet was collected and washed twice with ethanol (75% in water). The pellet was air-dried for about 15 min. The pellet was resuspended in 1 ml RNase-free dH$_2$O. The RNA concentration was calculated by determining the OD$_{260}$nm (1 OD$_{260}$nm =40 ug/ml).

3' RACE amplification of phytoene desaturase:

The literature was examined for nucleotide or amino acid sequences from plants or yeast encoding the gene for phytoene desaturase (See, Pecker et al., *Proc. Natl. Acad. Sci. USA*, Vol. 89, pp. 4962–4966 (1992), Hugueney et al., *Eur. J. Biochem.*, Vol. 209, pp. 399–407 (1992), Bartle et al., *Proc. Natl. Acad. Sci. USA*, Vol. 88, pp. 6532–6536 (1991)). Regions of conserved amino acid sequence were used to design suitable oligonucleotide primers for polymerase chain reaction (PCR) amplification. Appropriate primers were synthesized from these sequences on a DNA synthesizer or were obtained from commercial sources.

About 200 ng of total RNA was heated with 10 pg of Adapter Primer (Gibco BRL, Gaithersburg, Md.) for 10 min at 65° C. and then chilled 2 min on ice. The reaction mixture was made up to 20 ul total volume with final concentrations of 20 mM Tris-HCl (pH 8.4), 50 mM KCl, 2.5 mM MgCl$_2$, 100 ug/ml BSA, 10 mM DTT, 500 nM Adapter Primer and 0.5 mM each dATP, dCTP, dGTP and dTTP. The mixture was equilibrated 2 min at 42° C. 200 units of reverse transcriptase were added and the mixture incubated 30 min at 42° C. Two units of *E. coli* RNase H were added and the mixture incubated 10 min at 42° C. to yield the first strand cDNA.

The first strand cDNA was directly amplified by the PCR method. A 50 ul reaction was assembled with a final composition of 20 mM Tris-HCl (pH 8.4), 50 mM KCl, 2.5 mM MgCl$_2$, 100 ug/ml BSA, 200 nM Primer WPF10 (5'-ATGCCTCAAATTGGACTTGTTTCTGC-3'), 200 nM Universal Amplification Primer (Gibco BRL, Gaithersburg, Md.), 0.2 mM each dATP, dCTP, dGTP and dTTP, and 0.04 U/ul Taq DNA Polymerase. Amplification was in a DNA thermocycler with 1 cycle of 2 min at 94° C., 35 cycles of 10 sec at 94° C., 15 sec at 60° C., 90 sec at 72° C., and 1 cycle of 5 min at 72° C. Nested amplification was performed in a 50 ul reaction with a final composition of 10 mM Tris-HCl (pH 8.3), 50 mM KCl, 1.5 mM MgCl$_2$, 0.001% (w/v) gelatin, 0.2 mM each dATP, dCTP, dGTP and dTTP, 200 nM Universal Amplification Primer (Gibco BRL, Gaithersburg, Md.), 200 nM primer WPF11 (5'-GGTAGTTCAGCTTATCTTTGGAGC-3'), 1 ul PCR products (above), and 0.025 U/ul Taq DNA Polymerase. Amplification was in a DNA thermocycler with 1 cycle of 2 min at 94° C., 25 cycles of 10 sec at 94° C., 15 sec at 60° C., 90 sec at 72° C., and 1 cycle of 5 min at 72° C.

Southern Analysis of PCR Products:

Nested PCR 3' RACE products were analyzed by separation on a 1% agarose gel in TBE buffer (44.5 mM Tris-borate, 44.5 mM boric acid 1 mM EDTA). The PCR products in the gel were denatured by treatment for 20 min in 1.5M NaCl, 0.5 N NaOH and neutralized by soaking in several volumes of 1.5M NaCl, 1M Tris-HCl (pH 8.0). The PCR products were transferred to a nylon membrane and were UV-crosslinked.

Hybridization and detection of phytoene desaturase homologous sequences were performed using a chemiluminescent system. The membrane was prehybridized for 1 hr at 60° C. in 10 ml hybridization solution (5X SSC., 1X Blocking solution 0.1% N-laurylsarcosinate, 0.02% sodium dodecylsulfate (SDS); 10X Blocking solution is 10% (w/v) Blocking Reagent (Boehringer Mannhelm Biochemicals, Indianapolis, Ind.) in 100 mM maleic acid at pH 7.5, 150 mM NaCl). Incubations were in a rotating bottle hybridization incubator. Heat-denatured (5 min at 100° C.) probe was added to the prehybridization mixture at a final concentration of 1.25 ng/ml, and incubation of the resulting mixture was continued 4–16 hr at 60° C. The membrane was washed twice for 5 min in 2X SSC., 0.1% SDS at room temperature, and twice for 15 min in 0.1X SSC, 0.1% SDS at 60° C. For chemiluminescent detection the membrane was rinsed in 100 mM maleic acid, 150 mM NaCl, and incubated for 30 min at room temperature in 1X Blocking solution. Alkaline phosphatase-conjugated anti-digoxigenin Fab fragments were added (1:10,000 dilution), and incubation was continued for 30 min at room temperature. The membrane was washed twice for 15 min in 100 mM maleic acid, 150 mM NaCl, at room temperature. The membrane was equilibrated for 2 min in 100 mM Tris-HCl (pH 9.5), 100 mM NaCl, 50 mM $MgCl_2$. The membrane was placed on a sheet of clear acetate film and Lumi-Phos 530 (Boehringer Mannhelm Biochemicals, Indianapolis, Ind.) was added on the DNA side of the membrane. Another sheet of acetate film was used to cover the membrane, and the membrane was exposed to X-ray film. Positive signals on the X-ray film indicated the presence of PCR products containing phytoene desaturase homologous sequence.

Probe for phytoene desaturase was generated by random-primed labeling of a PCR fragment of the central region of tomato phytoene desaturase with digoxigenin-dUTP according to standard techniques. The PCR fragment was generated from tomato RNA by making a cDNA copy using Primer PDSI402X (5'-TGCTCGAGTGTGTTCT-TCAGTTTTCTGTCA-3') and Reverse Transcriptase, and then PCR amplification using Primer PDSF192 (5'-AACTC-GAGCGCTTTGATTTCTCCGAAGCTT-3') and Primer PDSI402X. The probe concentration was determined by comparison with a dilution series of a known standard on a nylon membrane and detection by chemiluminescence as above.

Cloning of the 3' RACE products:

The nested PCR 3' RACE products of phytoene desaturase were cloned using the pCRII vector (Invitrogen Corporation, San Diego, Calif.).

Clones were screened by digestion with EcoRI to liberate the insert, separation on an agarose gel, transfer to a nylon membrane, and hybridization and detection as described above. Clones exhibiting a positive hybridization signal were subjected to DNA sequence analysis using standard methods.

The sequence was examined for homology with the published phytoene desaturase sequences to confirm the identy of the phytoene desaturase.

5' RACE amplification of phytoene desaturase:

5' RACE (Gibco BRL) was used to generate 5' RACE products of phytoene desaturase. About 200 ng of total RNA from Nicotiana benthamiana or Nicotiana tabacum was heated with 2 pg of Primer WPF9, (5'-CTGCAGGTG-CAAAAACCAATTCC-3') for 5 min at 70° C. and then chilled 2 min on ice. The reaction mixture was made up to 20 ul total volume with final concentrations of 20 mM Tris-HCl (pH 8.4), 50 mM KCl, 2.5 mM $MgCl_2$, 100 ug/ml BSA, 10 mM DTT, 100 nM Primer WPF9 and 0.5 mM each dATP, dCTP, dGTP and dTTP. The mixture was equilibrated 2 min at 42° C. 200 units of reverse transcriptase was added and the mixture incubated 30 min at 42° C. The mixture was incubated 5 min at 55° C., two units of E. coli RNase H were added and the mixture incubated 10 min at 55° C. to yield the first strand cDNA. Excess primer was removed by purification with a GlassMAX™ (Gibco BRL) spun column. To the first strand cDNA reaction 95 ul of 6M NaI were added at room temperature. The mixture was transferred to a GlassMAX™ column and centrifuged 20 sec at 16,000 x g. The column was washed three times with 400 ul aliquots of ice cold wash buffer with 20 sec centrifugations. The column then was washed with a 400 ul aliquot of cold 70% ethanol and a 20 sec centrifugation. The cDNA was eluted with 50 ul of 65° C. $dH_2O$.

A poly (dC) tail was added to the cDNA. Ten ul of purified cDNA mixture plus 6 ul of $dH_2O$ was incubated 5 min at 70° C. then chilled on ice. The cDNA was assembled into a 20 ul reaction containing 10 mM Tris-HCl (pH 8.4), 25 mM KCl, 1.25 mM $MgCl_2$, 50 ug/ml BSA, 0.2 mM dCTP and 0.5 units/ul terminal deoxynucleotidyl transferase. After incubation for 10 min at 37° C., the terminal deoxynucleotidyl transferase was heat-inactivated 10 min at 70° C.

The dC-tailed cDNA was amplified by the PCR method. A 50 ul reaction was assembled with a final composition of 20 mM Tris-HCl (pH 8.4), 50 mM KCl, 2.5 mM $MgCl_2$, 100 ug/ml BSA, 400 nM primer PDSTK409 (5'-CT-TCAGTTTTCTGTCAAACC-3'), 400 nM Archor Primer (Gibco BRL, Gaithersburg, Md.), 0.2 mM each dATP, dCTP, dGTP and dTTP, and 0.04 U/ul Taq DNA Polymerase. Amplification was in a DNA thermocycler with 1 cycle of 2 min at 94° C., 35 cycles of 10 sec at 94° C., 15 sec at 55° C., 90 sec at 72° C., and 1 cycle of 5 min at 72° C. Nested amplification was performed in a 50 ul reaction with a final composition of 10 mM Tris-HCl (pH 8.3), 50 mM KCl, 1.5 mM $MgCl_2$ 0.001% (w/v) gelatin, 0.2 mM each dATP, dCTP, dGTP and dTTP, 200 nM Universal Amplification Primer, 200 nM primer WPF12 (5'-TCGGTTTGTGAC-CAGCATCTGCC-3'), 1 ul purified PCR products (above), and 0.025 U/ul Taq DNA Polymerase. Amplification was in a DNA thermocycler with 1 cycle of 2 min at 94° C., 25 cycles of 10 sec at 94° C., 15 sec at 55° C., 90 sec at 72° C., and 1 cycle of 5 min at 72° C.

Southern Analysis and cloning of PCR Products:

Nested PCR 5' RACE products of phytoene desaturase were analyzed and cloned as described previously with reference to the 3' RACE products.

Cloning of Phytoene Desaturase:

In many cases gene families are expressed in Nicotiana. Often such genes within a gene family are highly homologous, and as such, PCR strategies based upon primer sequences derived from conserved regions of a gene of interest are expected to amplify mRNA from each of the expressed genes.

The multiple allelic nature of some genetic loci in Nicotiana is of particular concern when cloning genes via 5' RACE and 3' RACE techniques. When assembling parts of the genetic sequence to create intact genes, the DNA sequences of the same allele were matched to avoid the generation of chimeric genes.

For *Nicotiana benthamina* and *Nicotiana tabacum* the overlapping sequence regions were compared to determine which of the alleles was represented by each cloned fragment. Appropriate 5' and 3' ends were merged into single clones to give full-length versions of the alleles.

DNA sequence was determined for the final constructs, and the sequence was translated in vitro using a rabbit reticulocyte lysate system to verify that the appropriate reading frame was maintained through the cloning steps. The protein products of the in vitro translation reactions were examined by polyacrylamide gel electrophoresis (PAGE) to determine that an appropriately sized product was produced.

The phytoene desaturase nucleic acid sequences provided from *Nicotioana benthamiana* have the sequences specified in SEQ ID NOS: 1 and 3, and the amino acid sequences encoded by those nucleic acid sequences are specified in SEQ ID NOS: 2 and 4.

The phytoene desaturase nucleic acid sequences provided from *Nicotiana tabacum* have the sequences specified in SEQ ID NOS: 5 and 7, and the amino acid sequences encoded by those nucleic acid sequences are specified in SEQ ID NOS: 6 and 8.

EXAMPLE 2:

Insertion of the full length sequence encompassing the coding region of the phytoene desaturase gene into a plant transformation vector with subsequent transformation and expression in transgenic plants was acomplished as follows: PCR amplification of *Nicotiana benthaminana* phytoene desaturase allele 1 coding with addition of appropriate restriction sites:

In order to facilitate the cloning of phytoene desaturase into a T-DNA vector, oligonucleotides were designed to exclude the 5' and 3' untranslated portions of the gene and to incorporate a SalI site at the 5' end of the gene and an SpeI site at the 3' end. The 5' end oligonucleotide was WPF17 (5'-CATACCGAGTCGACATGCC-3'). The 3' end oligonucleotide was WPF18 (5'AGTTCACTAGTCTAAAC-TACGC-3').

The coding region was amplified from plasmid pBSG800 (see FIG. 1) by the PCR method. A 50 ul reaction was assembled with a final composition of 1 ng template pBSG800, 20 mM Tris-HCl (pH 8.4), 50 mM KCl, 2.5 mM MgCl$_2$, 100 ug/ml BSA, 200 nM primer WPF17, 200 nM primer WPF18, 0.2 mM each dATP, dCTP, dGTP and dTTP, and 0.04 U/ul Taq DNA Polymerase. Amplification was with 1 cycle of 2 min at 94° C., 25 cycles of 10 sec at 94° C., 15 sec at 50° C., 120 sec at 72° C., and 1 cycle of 5 min at 72° C.

Cloning of the PCR product:

The PCR product was cloned. The phytoene desaturase coding region was excised from the clone by digestion with SalI and SpeI. The insert was separated from the vector on a 1% agorose gel, the band was excised from the gel, and the DNA isolated. The T-DNA cloning vector pKYLX-71 (See, Schardl, et al., *Gene*, Vol. 61, pp. 1–11 (1987)) was prepared by digestion with XhoI and XbaI. The insert was ligated into the vector using T4 DNA ligase and transformed into *E. coli*. The resulting plasmid was designated pBSG801.

Agrobacterium-mediated trnsformation of plants.

The above plasmid DNA (pBSG801) was isolated from *E. coli*. Plasmid DNA was introduced into *Agrobacterium tumefaciens* LBA4404 by electroporation. Transformants were selected on agar plates containing 5 ug/ml tetracycline.

Leaf disc transformation was used to introduce the T-DNA into *Nicotiana tabacura* and *Nicotiana benthamiana* using standard protocols (e.g., Fitzmaurice et al., *Plant Moleclar Biology*, Vol. 20, pp. 177–198 (1992)). Transformed shoots were selected on medium containing kanamycin. Shoots were excised, and placed in rooting medium containing kanamycin. When roots first appeared, plantlets were transferred into soil and grown to maturity.

EXAMPLE 3:

Inertion of the full length sequence encompassing the coding region of the phytoene desaturase gene into a virus-base gene expression system and expression in transfected plants was accomplished as follows:

Cloning of antisense phytoene desaturase into a TMV-based viral vector:

The phytoene desaturase gene can be transiently expressed in a plant using a virus-based gene delivery system. For example, the plasmid pBGC800 was digested with SalI and SpeI, and the insert fragment containing phytoene desaturase was separated from the vector fragment on an agarose gel. The fragment as excised from the gel, and the DNA as purified. The viral vector, a derivative of TB2 (Donson, et al., *Proc. Natl. Acad. Sci. USA.*, Vol. 88, pp. 7204—7208 (1991)) was prepared by digestion with XhoI and AvrII and separation on an agarose gel. The vector fragment was excised from the gel, and the DNA was purified. The viral vector and the phytoene desaturase fragment were ligated using T4 DNA ligase under standard conditions and transformed into *E. coli*.

A transcript of the viral vector containing antisense phytoene desaturase was synthesized using the SP6 RNA polymerase promoter site contained in the vector and employing SP6 RNA polymerase. The transcript was inoculated onto plants to establish an infection.

---

What is claimed is:

1. An isolated nucleotide molecule encoding a polypeptide which has enzymatic activity for producing zeta-carotene, which molecule is isolated from a Nicotiana species.

2. An isolated nucleotide molecule encoding a polypeptide which has enzymatic activity for producing zeta-carotene, which molecule encodes a polypeptide having an amino acid sequence selected from the group consisting of SEQ ID NO: 2, SEQ ID NO: 4, SEQ ID NO: 6 AND SEQ ID NO: 8.

3. An isolated nucleotide molecule encoding phytoene desaturase, said molecule having a nucleotide sequence which corresponds substantially to a member of the group consisting of SEQ ID NO: 1, SEQ ID NO: 3, SEQ ID NO: 5 and SEQ ID NO: 7.

4. The nucleotide molecule of claim 1 in the form of a DNA sequence.

5. The nucleotide molecule of claim 2 in the form of a DNA sequence.

6. The nucleotide molecule of claim 3 in the form of a DNA sequence.

7. The nucleotide molecule of claim 6 isolated from a Nicotiana species.

8. The nucleotide molecule of claim 7 isolated from *Nicotiana benthamiana*.

9. The nucleotide molecule of claim 7 isolated from *Nicotiana tabacura*.

10. The nucleotide molecule of claim 5 isolated from a Nicotiana species.

11. The nucleotide molecule of claim 10 isolated from *Nicotiana benthamiana*.

12. The nucleotide molecule of claim 10 isolated from *Nicotiana tabacura*.

13. An isolated nucleotide molecule encoding zeta-carotene selected from the group consisting of:

(a) isolated nucleotide molecules consisting essentially of the sequences specified by SEQ ID NO: 1; SEQ ID NO: 3, SEQ ID NO: 5 and SEQ ID NO: 7;

(b) isolated nucleotide molecules which hybridize to an isolated nucleotide molecule of (a) above under conditions represented by a wash stringency of 0.03M NaCl, 0.03M sodium citrate, and 0.1% SDS at 70° C., which are at least about 95% homologous to isolated nucleotide molecules of (a) above and which encode zeta-carotene; and (c) isolated nucleotide molecules which differ in sequence from the isolated nucleotide molecules of (a) and (b) above due to the degeneracy of the genetic code, and which encode zeta-carotene.

\* \* \* \* \*